US010350016B2

(12) United States Patent
Burbank et al.

(10) Patent No.: US 10,350,016 B2
(45) Date of Patent: Jul. 16, 2019

(54) STAPLER WITH CABLE-DRIVEN ADVANCEABLE CLAMPING ELEMENT AND DUAL DISTAL PULLEYS

(71) Applicant: Intuitive Surgical Operations, Inc., Sunnyvale, CA (US)

(72) Inventors: William A. Burbank, Sandy Hook, CT (US); Gregory W. Dachs, II, San Mateo, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 294 days.

(21) Appl. No.: 15/462,551

(22) Filed: Mar. 17, 2017

(65) Prior Publication Data

US 2017/0265954 A1 Sep. 21, 2017

Related U.S. Application Data

(60) Provisional application No. 62/309,828, filed on Mar. 17, 2016.

(51) Int. Cl.
*A61B 17/072* (2006.01)
*A61B 34/00* (2016.01)
(Continued)

(52) U.S. Cl.
CPC ............ *A61B 34/71* (2016.02); *A61B 17/068* (2013.01); *A61B 17/07207* (2013.01);
(Continued)

(58) Field of Classification Search
CPC ............... A61B 17/069; A61B 17/072; A61B 17/07207; A61B 17/00234;
(Continued)

(56) References Cited

U.S. PATENT DOCUMENTS 1,979,768 A  11/1934 Pearce
2,947,158 A   8/1960 King
(Continued)

OTHER PUBLICATIONS

Vertut, Jean and Phillipe Coiffet, Robot Technology: Teleoperation and Robotics Evolution and Development, English translation: Prentice-Hall, Inc.; Inglewood Cliffs, NJ, USA 1986, vol. 3A, 332 pages.

*Primary Examiner* — Scott A Smith
(74) *Attorney, Agent, or Firm* — Schwegman Lundberg & Woessner, P.A.

(57) ABSTRACT

A surgical instrument comprising: a jaw assembly; a slider beam; first and second distal jaw-mounted coaxial pulleys rotatably mounted to a distal portion of the second assembly; a two degree of freedom wrist that includes first and second pitch axis pulleys rotatable about a pitch axis and that includes a yaw pulley rotatable about a yaw axis; a first cable that is secured to the slider beam, that wraps about the first distal jaw-mounted pulley and that extends parallel to the jaw assembly to opposite sides of the first pitch axis pulley; a second cable that is secured to the slider beam, that wraps about the second distal jaw-mounted pulley and that extends parallel to the second jaw assembly to opposite sides of the second pitch axis pulley; and at least one yaw cable wrapped about at least a portion of the yaw pulley.

19 Claims, 17 Drawing Sheets

(51) Int. Cl.
*A61B 34/30* (2016.01)
*A61B 17/068* (2006.01)
*A61B 34/37* (2016.01)
*A61B 17/00* (2006.01)
*A61B 17/29* (2006.01)

(52) U.S. Cl.
CPC .............. *A61B 34/30* (2016.02); *A61B 34/37* (2016.02); *A61B 17/072* (2013.01); *A61B 2017/00477* (2013.01); *A61B 2017/07214* (2013.01); *A61B 2017/07278* (2013.01); *A61B 2017/07285* (2013.01); *A61B 2017/2927* (2013.01); *A61B 2017/2937* (2013.01); *A61B 2034/715* (2016.02)

(58) Field of Classification Search
CPC ...... A61B 17/00491; A61B 2017/2927; A61B 2017/2926; A61B 2017/07214; A61B 2017/07278; A61B 2017/07285; A61B 2034/305; A61B 34/30; A61B 34/71
USPC .............. 227/19, 175.1, 176.1, 175.2, 180.1; 606/139, 153, 219, 1, 208, 170
See application file for complete search history.

(56) References Cited

U.S. PATENT DOCUMENTS

| | | | |
|---|---|---|---|
| 4,605,001 A | 8/1986 | Rothfuss et al. | |
| 4,608,981 A | 9/1986 | Rothfuss et al. | |
| 5,507,426 A | 4/1996 | Young et al. | |
| 5,632,432 A * | 5/1997 | Schulze | A61B 17/07207 227/176.1 |
| 5,657,921 A | 8/1997 | Young et al. | |
| 5,797,900 A | 8/1998 | Madhani et al. | |
| 6,250,532 B1 * | 6/2001 | Green | A61B 17/07207 227/175.1 |
| 6,436,107 B1 * | 8/2002 | Wang | A61B 1/00149 318/568.11 |
| 6,491,701 B2 * | 12/2002 | Tierney | G16H 40/63 606/130 |
| 6,902,560 B1 * | 6/2005 | Morley | A61B 17/062 606/1 |
| 6,953,139 B2 | 10/2005 | Milliman et al. | |
| 7,695,485 B2 * | 4/2010 | Whitman | A61B 17/07207 606/170 |
| 7,726,537 B2 * | 6/2010 | Olson | A61B 17/07207 227/175.1 |
| 7,963,433 B2 * | 6/2011 | Whitman | A61B 17/07207 227/178.1 |
| 8,105,320 B2 * | 1/2012 | Manzo | A61B 17/3201 606/1 |
| 8,348,123 B2 | 1/2013 | Scirica et al. | |
| 8,496,153 B2 | 7/2013 | Demmy et al. | |
| 8,523,900 B2 * | 9/2013 | Jinno | A61B 17/29 606/208 |
| 8,600,551 B2 * | 12/2013 | Itkowitz | G09B 23/285 700/245 |
| 8,602,288 B2 * | 12/2013 | Shelton, IV | A61B 17/068 227/176.1 |
| 8,640,788 B2 | 2/2014 | Dachs, II et al. | |
| 8,684,253 B2 * | 4/2014 | Giordano | A61B 17/00234 227/180.1 |
| 8,852,174 B2 | 10/2014 | Burbank | |
| 8,876,857 B2 | 11/2014 | Burbank | |
| 8,911,428 B2 * | 12/2014 | Cooper | A61B 17/00234 606/1 |
| 8,915,940 B2 * | 12/2014 | Steege | A61B 17/29 606/205 |
| 8,991,678 B2 | 3/2015 | Wellman et al. | |
| 8,992,565 B2 | 3/2015 | Brisson et al. | |
| 9,060,678 B2 * | 6/2015 | Larkin | A61B 1/00087 |
| 9,072,535 B2 * | 7/2015 | Shelton, IV | A61B 17/07207 |
| 9,125,662 B2 * | 9/2015 | Shelton, IV | A61B 18/1445 |
| 2007/0187453 A1 * | 8/2007 | Smith | A61B 17/07207 227/175.1 |
| 2009/0283568 A1 * | 11/2009 | Racenet | A61B 17/07207 227/181.1 |
| 2012/0080498 A1 * | 4/2012 | Shelton, IV | A61B 17/00491 227/178.1 |
| 2013/0267950 A1 | 10/2013 | Rosa et al. | |
| 2015/0230794 A1 | 8/2015 | Wellman et al. | |

* cited by examiner

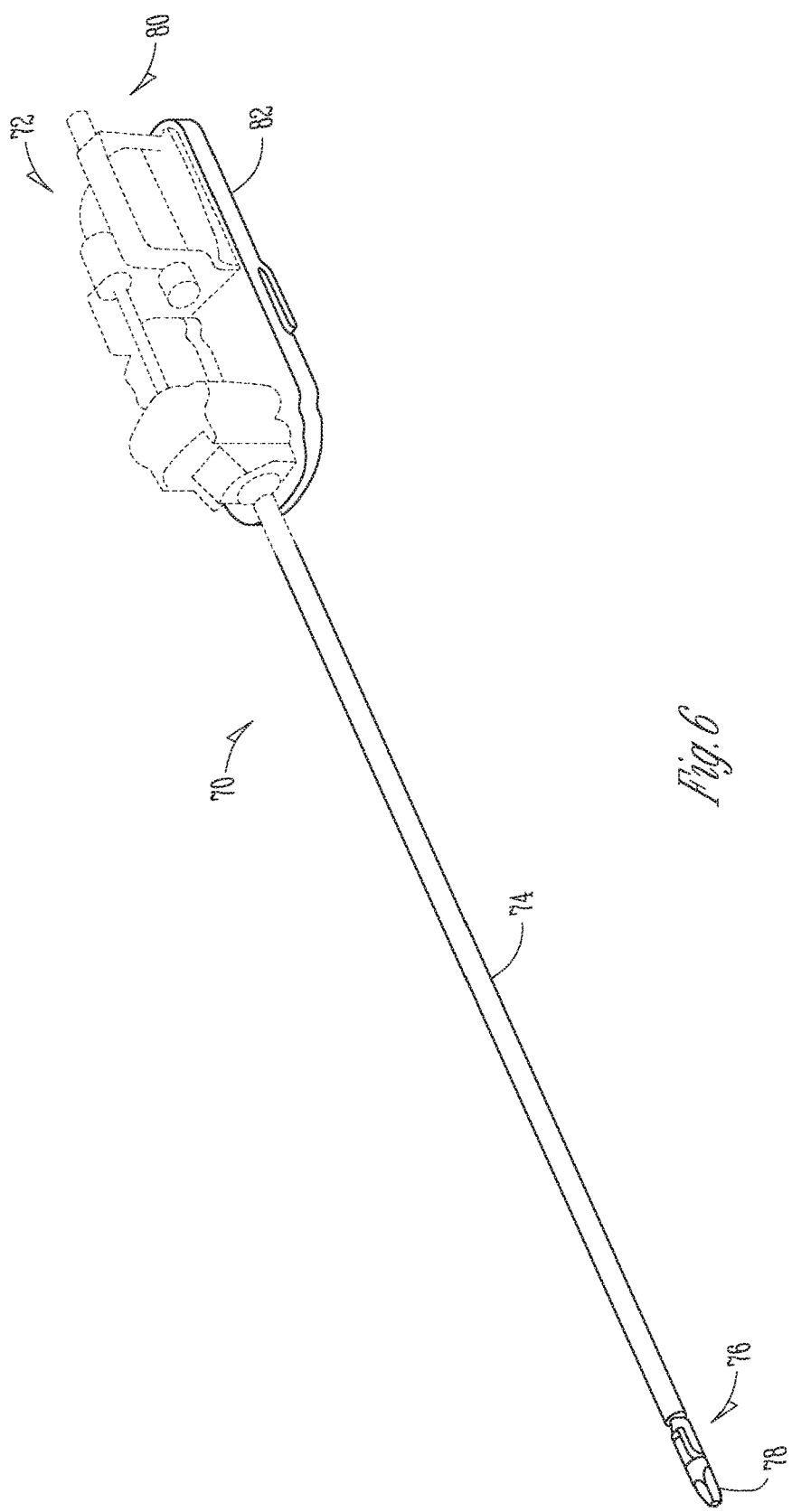

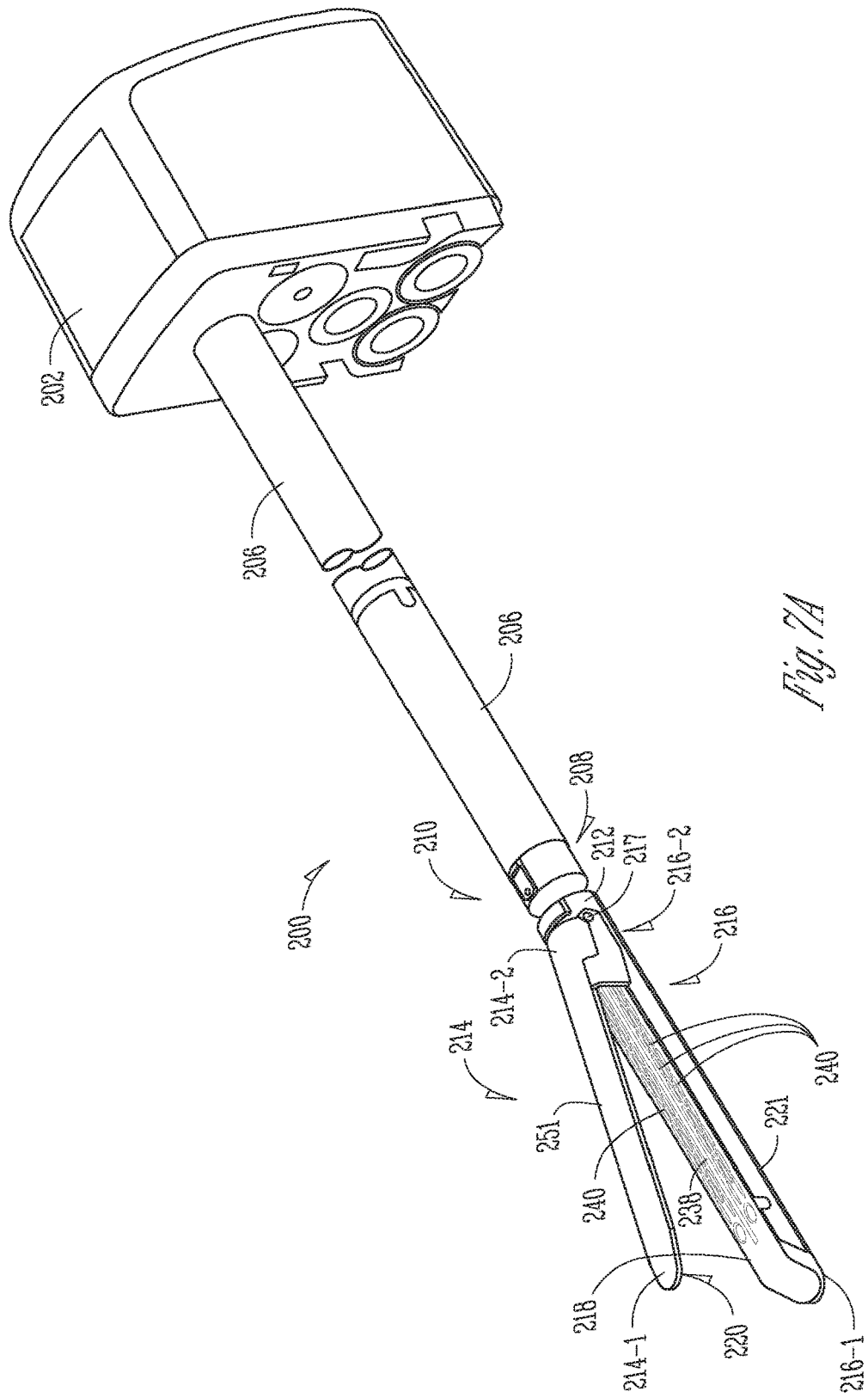

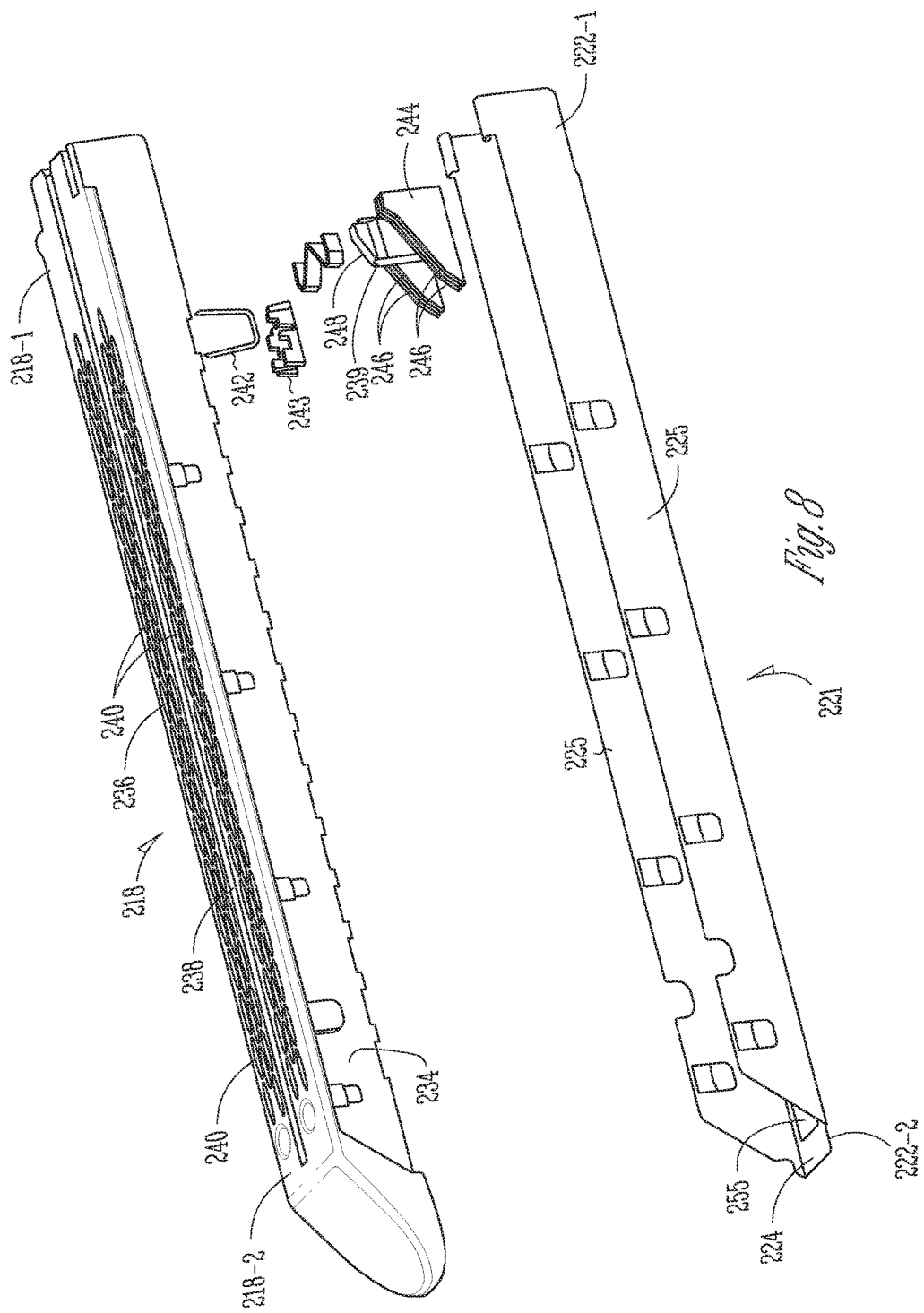

STAPLER WITH CABLE-DRIVEN ADVANCEABLE CLAMPING ELEMENT AND DUAL DISTAL PULLEYS

CLAIM OF PRIORITY

This application claims the benefit of priority under 35 U.S.C. § 119(e) to U.S. Provisional Patent Application Serial No. 62/309,828, filed on Mar. 17, 2016, which is incorporated by reference herein in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

Minimally invasive teleoperated surgical systems have been developed to increase a surgeon's dexterity when working on an internal surgical site, as well as to allow a surgeon to operate on a patient from a remote location (outside the sterile field). In a teleoperated surgical system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

SUMMARY

In one aspect, a surgical instrument includes a jaw assembly, a slider beam and first and second distal jaw-mounted coaxial pulleys rotatably mounted to a distal portion of the jaw assembly. The jaw depends from a two degree of freedom wrist that includes first and second pitch axis pulleys rotatable about a pitch axis. First and second pitch/slider cables impart longitudinal forces to the slider beam and impart rotational forces to the first and second pitch axis cables. As the first pitch/slider cable moves longitudinally along the second jaw in either a proximal direction or a distal direction or remains stationary in response to a force imparted to it, the first pitch/slider cable imparts a clockwise or counter-clockwise rotational force upon the first pitch axis pulley. Similarly, as the second pitch/slider cable moves longitudinally along the second jaw in either a proximal direction or a distal direction or remains stationary in response to a force imparted to it, the second pitch/slider cable imparts a clockwise or counter-clockwise rotational force upon the second pitch axis pulley.

BRIEF DESCRIPTION OF DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 6 is an illustrative drawing showing an example surgical tool in accordance with some embodiments.

FIG. 7A is an illustrative perspective drawing of a surgical tool assembly with a jaw assembly end effector that includes first and second jaws shown in an open position in accordance with some embodiments.

FIG. 8 is an illustrative exploded view of a partial second jaw in accordance with some embodiments.

DESCRIPTION OF EMBODIMENTS

Figure 1:
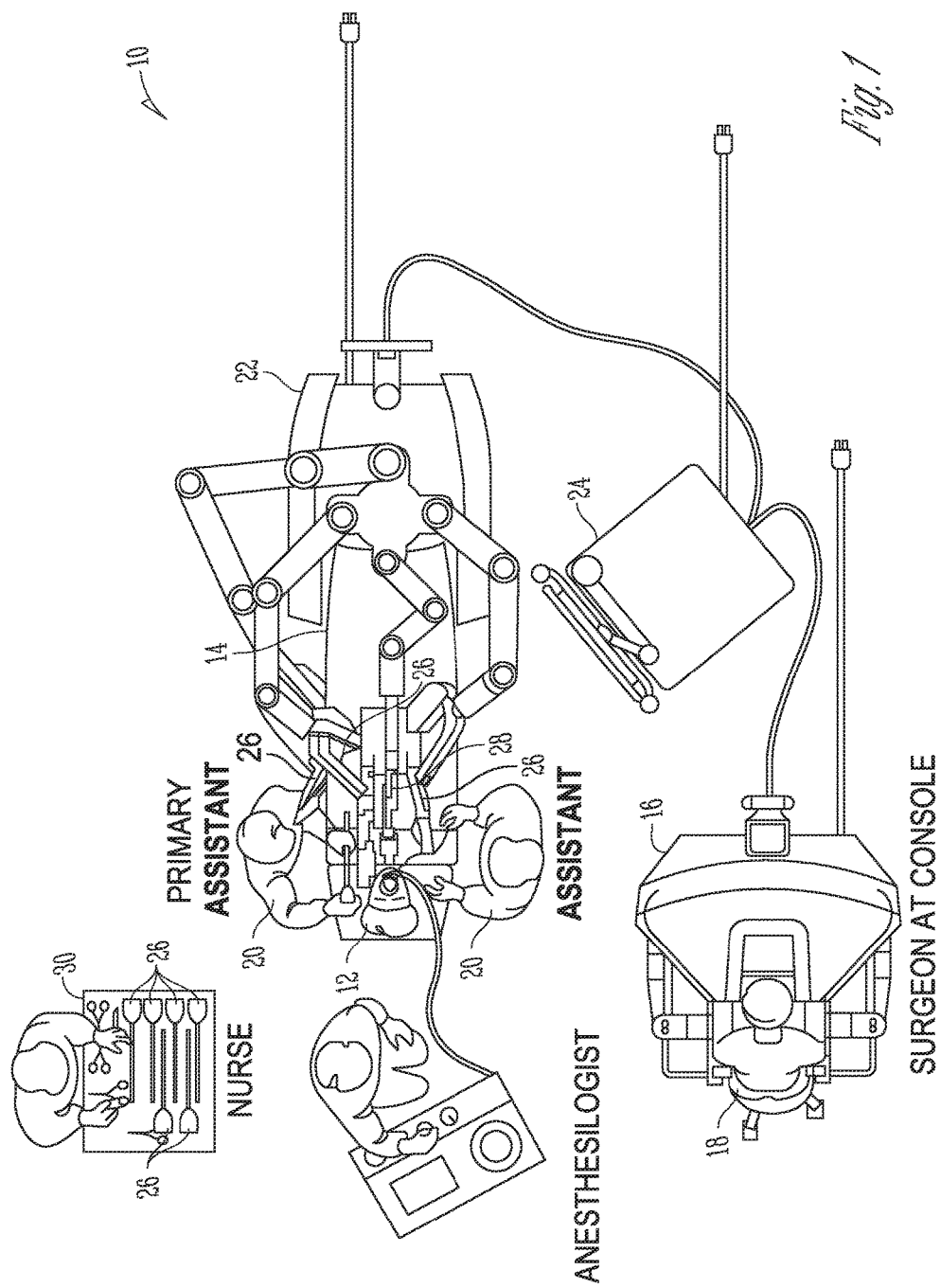
FIG. 1 is an illustrative plan view illustration of a teleoperated surgical system in accordance with some embodiments.

The following description is presented to enable any person skilled in the art to create and use a cable driven i-beam within a surgical stapler. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. In the following description, orientation of certain components are described relative to their orientations as shown in the illustrative drawings as top, bottom and vertical and is not intended to be limiting. Thus, the inventive subject matter is not intended to be limited to the embodiments shown, but is to be accorded the widest scope consistent with the principles and features disclosed herein.

Surgical System Overview

Referring now to the drawings, in which like reference numerals represent like parts throughout the several views, FIG. 1 is an illustrative plan view of a teleoperated surgical system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient Side Cart 22 and an Electronics Cart 24. The Patient Side Cart 22 can manipulate at least one removably coupled tool assembly 26 (hereinafter also referred to as a "tool") through a minimally invasive incision in the body of the Patient 12 while the Surgeon 18 views the surgical site through the Console 16. An image of the surgical site can be obtained by an imaging device 28 (sometimes called "endoscope 28," such as in situations where an endoscope can be used as the imaging device) such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors.

Figure 2:
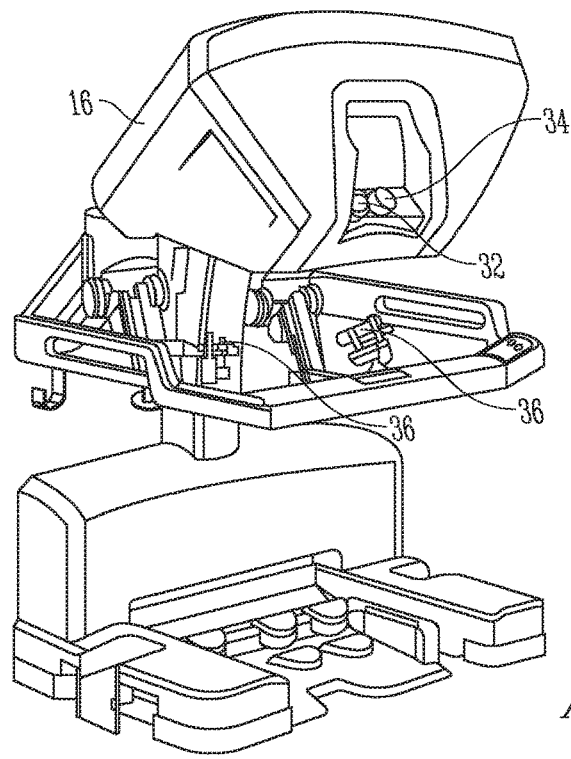
FIG. 2 is an illustrative perspective view of the Surgeon's Console in accordance with some embodiments.

FIG. 2 is an illustrative perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

Figure 3:
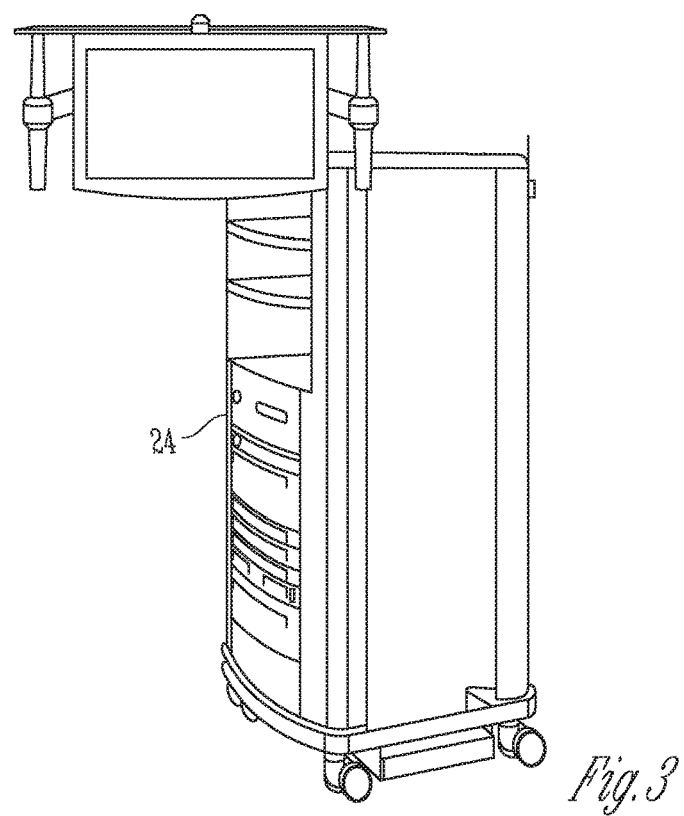
FIG. 3 is an illustrative perspective view of e Electronics Cart in accordance with some embodiments.

FIG. 3 is an illustrative perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope.

Figure 4:
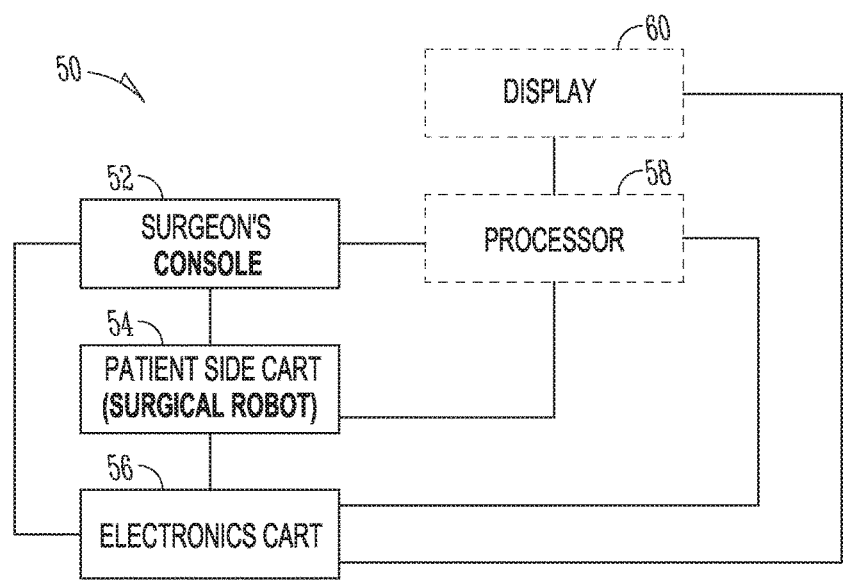
FIG. 4 is an illustrative block diagram diagrammatically representing functional relationships among components of a teleoperated surgery system in accordance with some embodiments.

FIG. 4 is an illustrative block diagram diagrammatically representing functional relationships among components of a teleoperated surgery system 50 (such as surgical system 10 of FIG. 1). As discussed above, a Surgeon's Console 52 (such as Surgeon's Console 16 in FIG. 1) can be used by a Surgeon to control a Patient Side Cart (also called "Surgical Robot" when the Patient Side Cart is a Surgical Robot) 54 (such as Patient Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
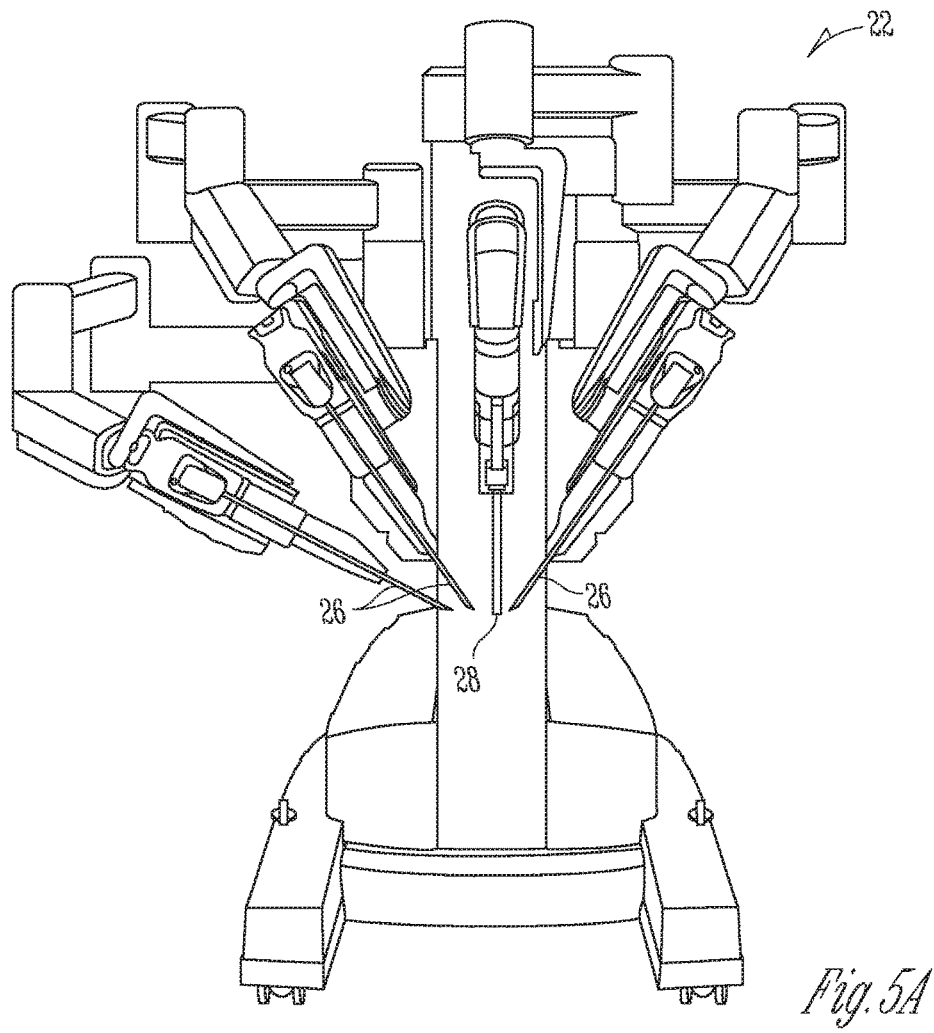
FIGS. 5A-5B are illustrative drawings showing a Patient Side Cart and a surgical tool 62, respectively in accordance with some embodiments.
Figure 5B:
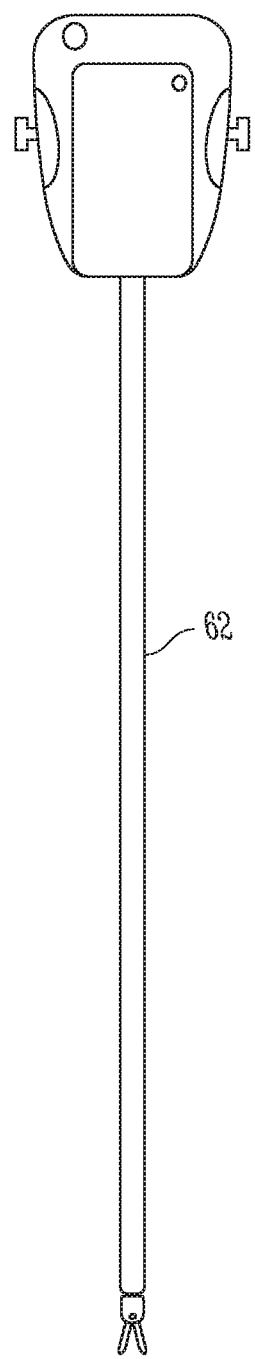

FIGS. 5A-5B are illustrative drawings showing a Patient Side Cart 22 and a surgical tool 62, respectively in accordance with some embodiments. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by teleoperated mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

FIG. 6 is an illustrative drawing showing an example surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Jaw Assembly

FIG. 7A is an illustrative perspective drawing of a surgical tool assembly 200 with a jaw assembly end effector 210 (also called "jaw assembly 210") that includes first and second jaws 214, 216 shown in an open position in accordance with some embodiments. The tool assembly 200 includes a proximal actuation assembly 202, a main shaft 206, a two degree of freedom (2-dof) wrist 208, shown in partial cutaway, and the jaw assembly end effector 210. The jaw assembly 210 includes a base 212 coupled to a distal side of the 2-dof wrist 208, a first jaw 214 and a stationary second jaw 216. The first jaw 214 is articulable. The first jaw 214 has a distal end 214-1 and a proximal end 214-2. The second jaw 216 also has a distal end 216-1 and a proximal end 216-2. In operation, the base 212 is an integral part of the proximal end 216-2 of the second jaw 216. The base 212 includes a pivot pin 217, which includes a jaw rotation axis 217-1, that is secured between the base 212 and a proximal end of the first jaw 214, about which a proximal end of the first jaw 214 pivots to achieve opening and closing movement of the first jaw 214 relative to the second jaw 216. In an open position shown in FIG. 7A, the first jaw 214 is rotated to a position in which distal ends 214-1, 216-1 of the first and second jaws 214, 216 are spaced apart so that the jaws can be more easily maneuvered within a surgical site to encompass anatomical tissue (not shown) between them without actually clamping the tissue in place between them.

The jaw assembly end effector 210 includes a surgical stapler. The second jaw 216 includes an elongated stapler cartridge 218 seated within a stapler cartridge support channel structure 221 configured to support the cartridge 218. The stapler cartridge 218 carries fasteners, e.g., staples, to be used to attach tissue during a surgical procedure. The stapler cartridge 218 defines a central longitudinal cartridge slot 238 that extends through the cartridge 218 and extends along substantially its entire length. The stapler cartridge 218 also defines multiple laterally spaced rows of staple retention slots 240 that extend longitudinally along one side of the first cartridge slot 238 and defines multiple laterally rows of spaced staple retention slots 240 that extend longitudinally along an opposite side of the first cartridge slot 238. Each staple retention slot 240 is sized to receive a staple (not shown).

The proximal actuation assembly 202 multiple motors (not shown) operatively coupled to impart forces to cables and/or with hypotubes that extend within the main shaft 206 to effect pitch and yaw movement to the wrist 208 and to effect opening or closing of the jaw assembly 210. More particularly, the proximal actuation assembly 202 includes motors configured to impart tension forces to cables that engage surfaces within the wrist 208 to selectively reorient the jaw assembly 210 relative to the main shaft 206 in two dimensions, referred to as pitch and. yaw. Moreover, the proximal actuation assembly 202 includes motors configured to impart tension forces to cables that engage surfaces within the jaw assembly 210 to actuate one or more jaw assembly features, such as rotation of the first jaw 214 about the pivot pin 217 to open and close the first jaw 214 relative to the base 212 and the second jaw 216 and to move an a slider beam (not shown) longitudinally within the longitudinal cartridge slot 238. In accordance with some embodiments, control cables (not shown) are used to operatively couple the actuation assembly 202 with the wrist 208 and with the jaw assembly 210. The control cables include flexible cable segments coupled with rigid hypotube segments within the main shaft 206 that are routed between the actuation assembly 202 and the wrist 208 and the jaw assembly 210 through a bore of the main shaft 206.

Figure 7B:
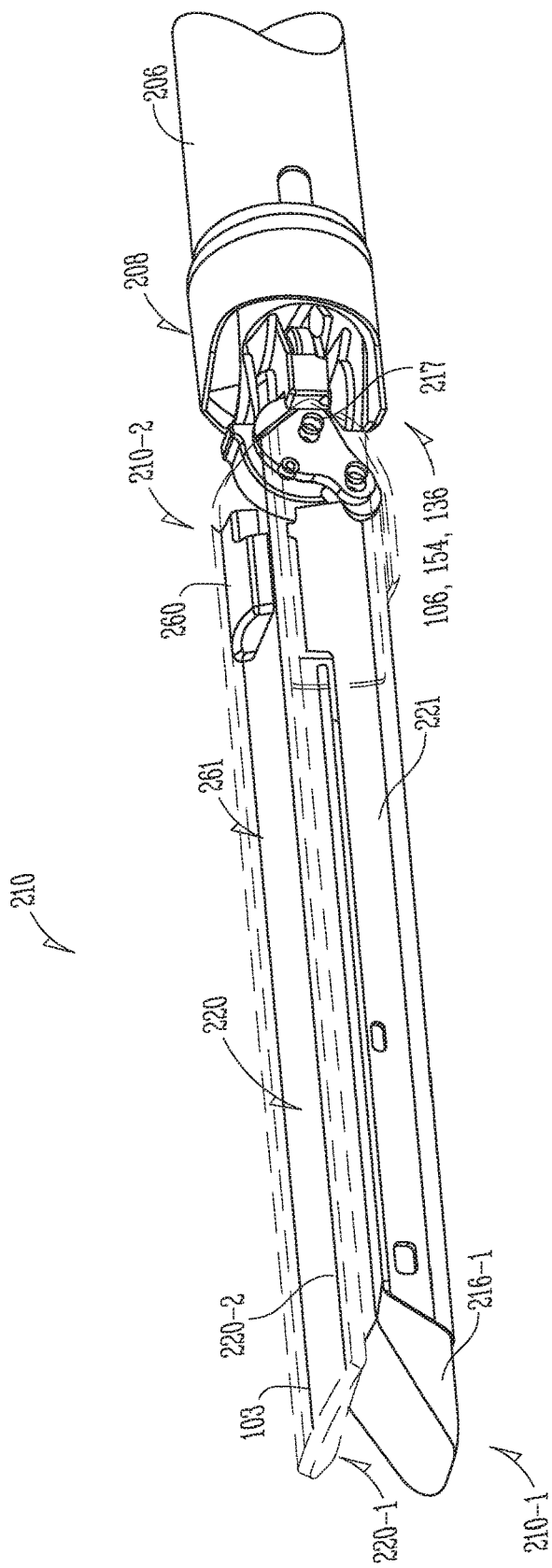
FIG. 7B is an illustrative partial perspective drawing of the surgical tool assembly of FIG. 7A with the first and second jaws in a closed position in accordance with some embodiments.

In a closed position shown in FIG. 7B, the first and second jaws are disposed parallel to each other spaced apart by an amount to accommodate anatomical tissue (not shown) that may be clamped between them. The first jaw 214 includes an anvil 220 having a first (inner) anvil surface 220-1 that faces the second jaw 216 and a second (outer) surface 220-2 that faces away from the second jaw 216. In operation, staples are deformed against the first anvil surface 220-1 to staple together tissue (not shown) disposed between the first and second jaws 214, 216. An outer first jaw cover 251, shown transparent with dashed lines in FIG. 7B, overlays a back side of the anvil 220 so that the anvil second surface 220-2 and the outer first jaw cover 251 together define an enclosed first jaw channel 261 between them. The anvil portion of the first jaw defines a first longitudinal slot 253. A cross-beam portion 258 (not shown) of a cable driven slider beam 104, which is discussed more fully below, extends through the first slot 253, and a first transverse beam portion 260 of the cable driven slider beam 104 (not shown) is shown disposed within the first jaw channel 261 in contact with the second (outer) anvil surface 220-2, in accordance with some embodiments.

FIG. 8 is an illustrative exploded view of a partial second jaw 216 in accordance with some embodiments. The second jaw 216 includes the support channel structure 221, which includes a proximal end 221-1 (also "proximal end portion 221-1") and a distal end 221-2 (also "distal end portion 221-2"). The support channel structure 221 includes the sidewalls 225 and a bottom wall 224, which defines a second elongated longitudinal slot 255, only a small distal portion of which is visible. The cross-beam portion 258 (not shown) of the cable driven slider beam 104 (not shown), extends through the second slot 255, and a second transverse beam portion 262 is shown disposed in contact with an outward facing surface of the bottom wall 224. The elongated cartridge 218 includes a proximal end 218-1 and a distal end 218-2. The cartridge includes cartridge outer sidewalls 234 and an upper surface 236. The upper surface 236 faces the anvil 220 of the first jaw 214. The upper surface 236 of the cartridge 218 defines a central first longitudinal cartridge slot 238 that extends through the cartridge 218 and that is aligned with the second longitudinal cam slot 255 when the cartridge 218 is disposed within the support channel structure 221. The cartridge upper surface portion includes inner opposed facing sidewalls 238-1, 238-2 that define the cartridge slot 238 sized to receive the cross-beam portion 258 of the slider beam 104 (not shown) and act as a cam surfaces to guide the slider beam 104 longitudinally along the longitudinal length of the second jaw 216. The upper surface 236 also defines multiple rows of longitudinally spaced staple retention slots 240 that extend longitudinally along one side of the first cartridge slot 238 and defines multiple rows of longitudinally spaced staple retention slots 240 that extend longitudinally along opposite sides of the first cartridge slot 238. Each staple retention slot 240 is sized to receive a fastener 242 (also "staples 242" where the fasteners shown are staples) and a staple pusher 243, which includes a plurality of inclined upstanding cam wedges 246 and a knife edge 248 upstanding between and proximal to the cam wedges 246. The cartridge 218 defines multiple longitudinal slots (not shown) in its underside along which the cam wedges 246 can slide with the knife upstanding from and sliding within the first cartridge slot 238. Alternatively, in accordance with some embodiments, a knife (not shown) can be secured to the slider beam 104 (not shown) described below.

During operation of surgical stapler-type jaw assembly end effector 210, the slider beam 104 (not shown) disposed proximal to the pusher shuttle 244 is moved in a distal direction within the second jaw 216, pushing the pusher shuttle 244 in front of it. As the pusher shuttle 244 moves distally along the second jaw 216, the cam wedges 246 move into sequential contact with pushers 243 within the longitudinally spaced retention slots 240, to cause pushers 243 to translate vertically within retention slots 240, and to urge fasteners 242 from retention slots 240 into the staple deforming cavities (not shown) formed within the anvil 220 of the first jaw 214. As the pusher shuttle 244 translates longitudinally, it pushes up fasteners 242, which are deformation against the anvil 220. Meanwhile, the knife edge 248 upstands through the first cartridge slot 238 and cuts tissue between tissue regions stapled through action of the cam wedges 246, fasteners 242 and the anvil 220. U.S. Pat. No. 8,991,678 (filed Oct. 26, 2012) issued to Wellman et at, which is incorporated herein in its entirety by this reference, discloses a surgical stapler cartridge and its operation.

Figure 9:
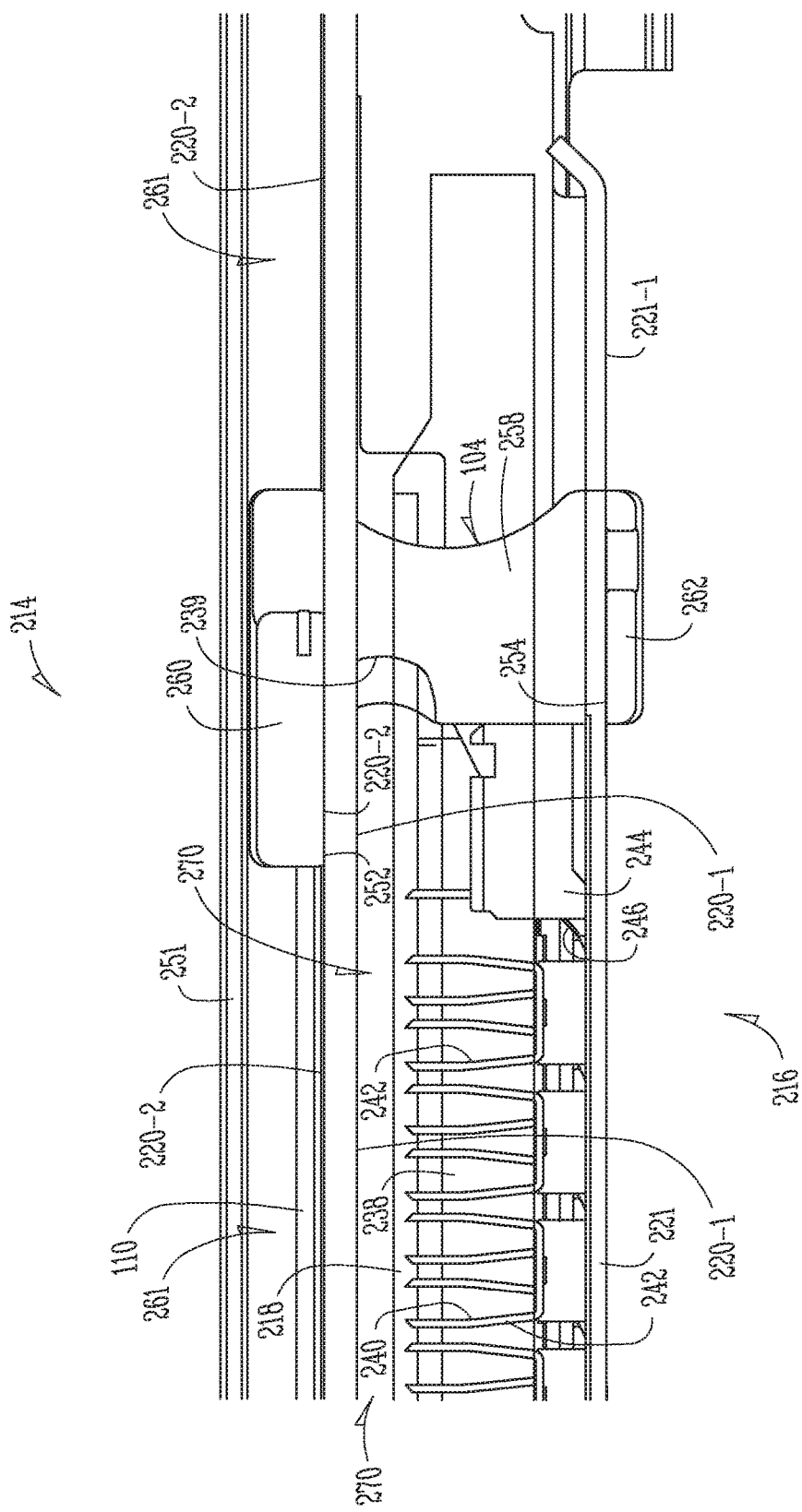
FIG. 9 is an illustrative cross-sectional side view of proximal portions of the first and second jaws in a closed position, in accordance with some embodiments.

FIG. 9 is an illustrative cross-sectional side view of proximal portions of the first and second jaws 214, 216 in a closed position, in accordance with some embodiments. The first and second jaws 214, 216 extend parallel to each other with a space 270 between them that is wide enough to capture and clamp tissue between them. The cartridge 218 is shown with staples 242 housed in retention the slots 240 therein. The cable driven slider beam 104 is shown having a cross-beam portion 258 having first and second transverse beam portions 260, 262 mounted on opposite ends thereof. The cross-beam portion 258 is slidably mounted within the cartridge slot 238, and the cartridge 218 disposed between the first and second transverse beam portions 260, 262.

Cables Wrapped About Distal Jaw-Mounted Pulleys to Drive the Slider Beam

Figure 10:
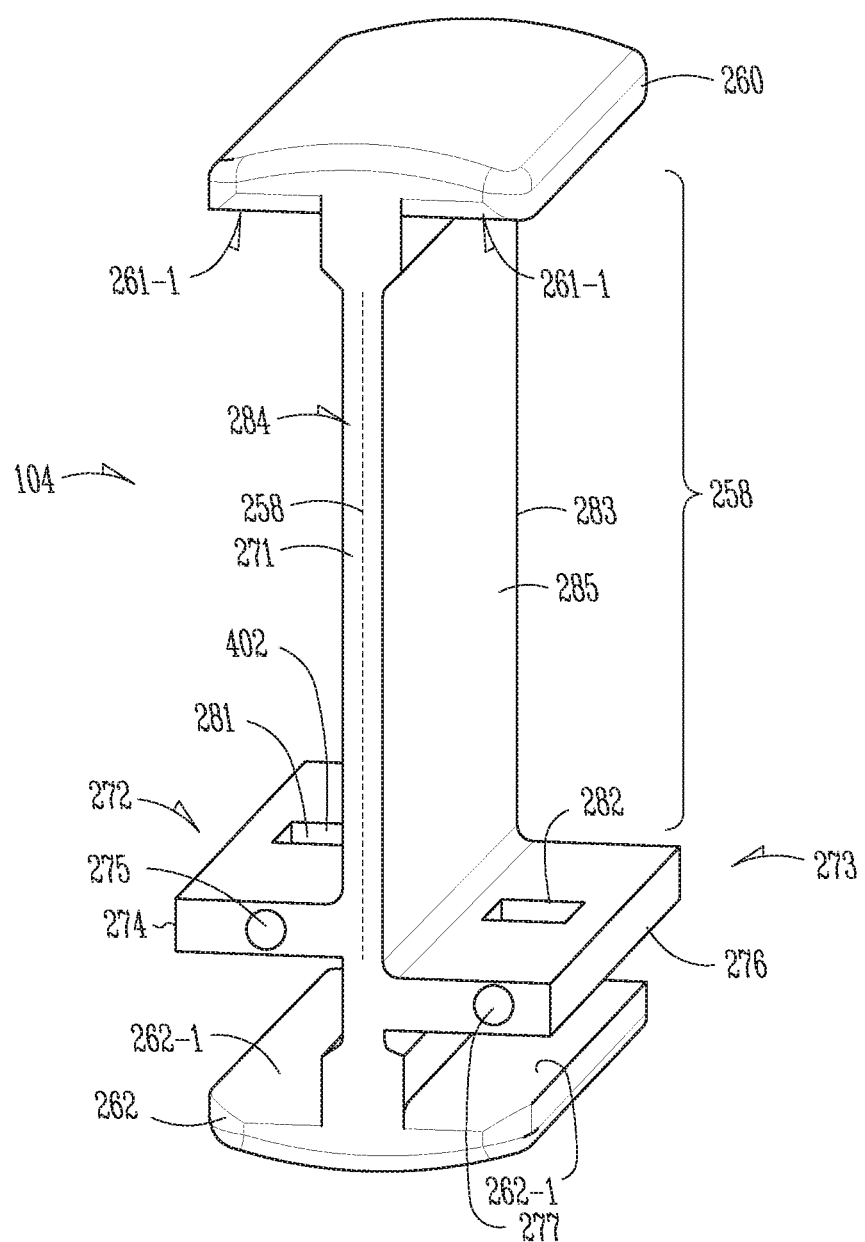
FIG. 10 is an illustrative perspective view of the slider beam in accordance with some embodiments.

FIG. 10 is an illustrative perspective view of the slider beam 104 in accordance with some embodiments. The slider beam 104 has an i-beam contour that includes a cross-beam portion 258, a first transverse beam portion 260 secured to a first end of the cross-beam portion 258, and a second transverse beam 262 secured to a second end of the cross-beam 258 portion. In operation, the cross-beam portion 258 is cable-driven to follow a path defined by the cartridge slot 238 while its leading edge 271 pushes the staple pusher 244 in front of it. Moreover, as explained more fully below the transverse beam end portions 260, 262 cooperate to clamp the first and second jaws 214, 216 while the staple pusher 244 is pushed along the length of the jaw assembly 210. The cross-beam portion 258 is sized to slidably fit simultaneously within a first elongated slot 253 defined by the anvil 220 and the second elongated slot 255 defined by the bottom wall 224 of the cartridge support channel structure 221. The first transverse beam portion 260 extends laterally outward from opposed sides of the cross-beam portion 258 so as to define a first inward facing surfaces 260-1 that acts as a first jaw cam follower. The second transverse beam portion 262 extends laterally outward from opposed sides of the cross-beam portion 258 so as to define a second inward facing surfaces 262-1 that acts as a second jaw cam follower. Together, the first and second transverse beam portions 260, 262 cooperate to exert a clamping force that urges the first and second jaws 214, 216 together as cross-beam portion 258 of the slider beam 104 pushes the staple pusher 244 longitudinally from a proximal end of the jaw assembly 210 to its distal end.

The cross-beam portion 258 includes the leading edge 271, a trailing edge 283 (not visible), a first planar side face 284 (not visible) and opposite-facing planar second side face 285. The beam portion defines a median plane represented by dashed line 278 shown on the leading edge 271 which extends through the center of the cross-beam portion 258 parallel to the first planar side face 284 (not visible) and the opposite-facing planar second side face 285. When the cross-beam portion 258 moves longitudinally along the second jaw 216, the median plane 278 of the cross-beam portion 258 follows the center axis 265 of the second elongated slot 255 shown in FIG. 13 described more fully below.

A first protrusion 272 extends laterally outward from the first side face 284 of the cross-beam portion 258. A second protrusion 273 extends laterally outward from the opposite-facing second side face 285 of the cross-beam portion 258. The first protrusion 272 includes a surface for attachment of a first cable segment 110. The first cable segment 110 also may be referred to herein as a first 'pitch/slider' cable segment 110. The second protrusion 273 includes a surface for attachment of a second cable segment 112. The second cable 112 segment also may be referred to herein as a second 'pitch/slider' cable segment 112. More specifically, the first protrusion 272 includes a first cantilever beam 274 that extends laterally outward from the first side face of the cross-beam portion 258 and that defines a first channel 275 therethrough that is sized to receive the first pitch/slider cable segment 110. The second protrusion 273 includes a second cantilever beam 276 that extends laterally outward from the second side face of the cross-beam portion 258 and that defines a second channel 277 therethrough that is sized to receive the second pitch/slider cable segment 112. A first crimp opening 281 is formed in the first cantilever beam 274 transverse to the first channel 275. The first crimp opening 281 is bounded by a first crimp surface 402 to engage a crimp (not shown) in the first cable 110 to fixedly secure the first cable 110 to the first cantilever beam 274. A second crimp opening 282 is formed in the second cantilever beam 276 transverse to the second channel 277. The second crimp opening 282 is bounded by a second crimp surface 404 to engage a crimp (not sown) in the second cable 112 to fixedly secure the second cable 112 to the second cantilever beam 276. The first and second cantilever beams 274, 276 are vertically offset from one another by a vertical offset distance that matches a vertical offset distance between the co-axial top and bottom jaw-mounted pulleys 310, 312, described below. It will be appreciated that although in one embodiment, the first pitch/slider cable 110 includes a single unitary cable secured at the first crimp surface 402 to the first cantilever beam 274, in an alternative embodiment, the first pitch/slider cable 110 includes two segments, extending longitudinally from opposite sides of the first cantilever beam 274. Similarly, although in one embodiment, the second pitch/slider cable 112 includes a single unitary cable secured at the second crimp surface 404 to the second cantilever beam 276, in an alternative embodiment, second first pitch/slider cable 112 includes two segments, extending longitudinally from opposite sides of the second cantilever beam 276.

Figure 11:
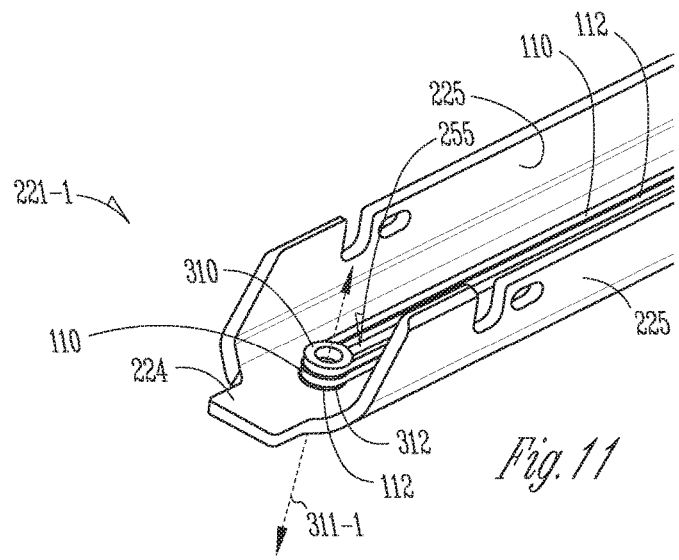
FIG. 11 is an illustrative perspective view of a distal end portion of a stapler cartridge support channel structure of a second jaw with the pair of a coaxial distal end jaw mounted pulleys in accordance with some embodiments.
Figure 12:
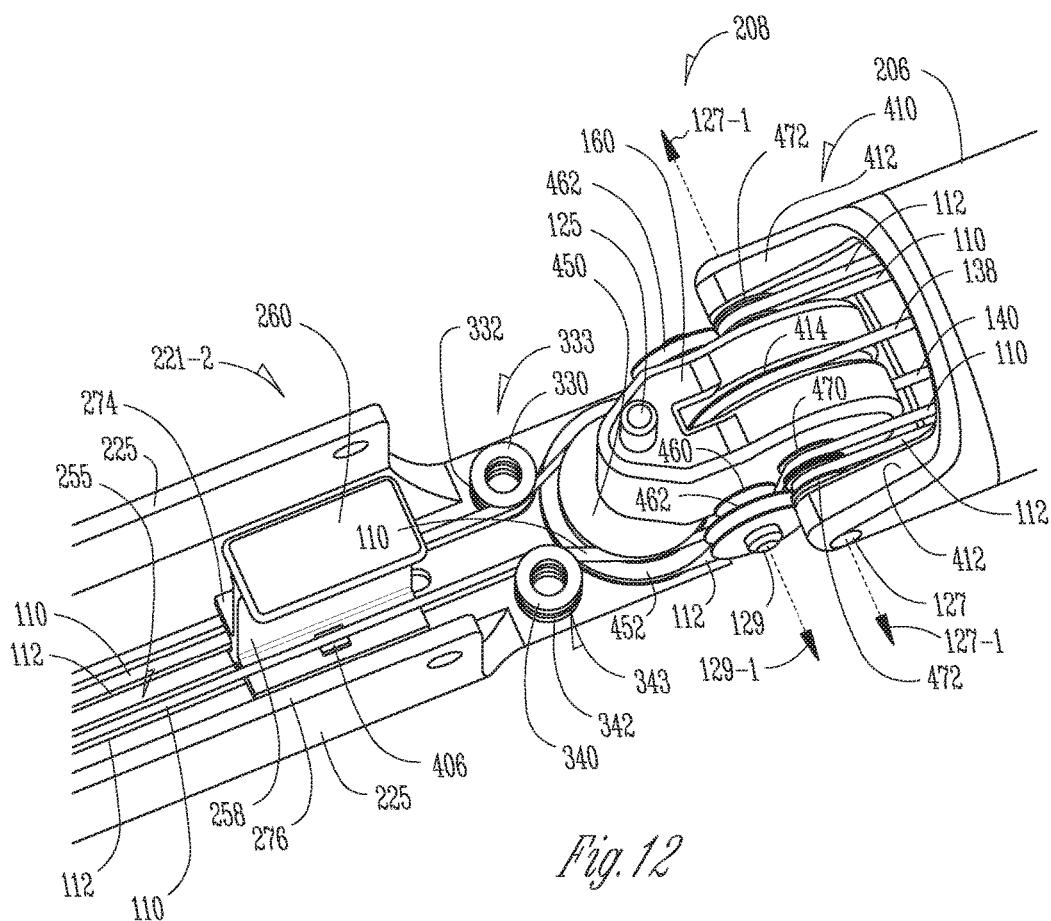
FIG. 12 is an illustrative top perspective view of a proximal end portion of stapler cartridge support channel structure of a second jaw, showing first and second pairs of coaxial proximal end jaw mounted pulleys in accordance with some embodiments.
Figure 13:
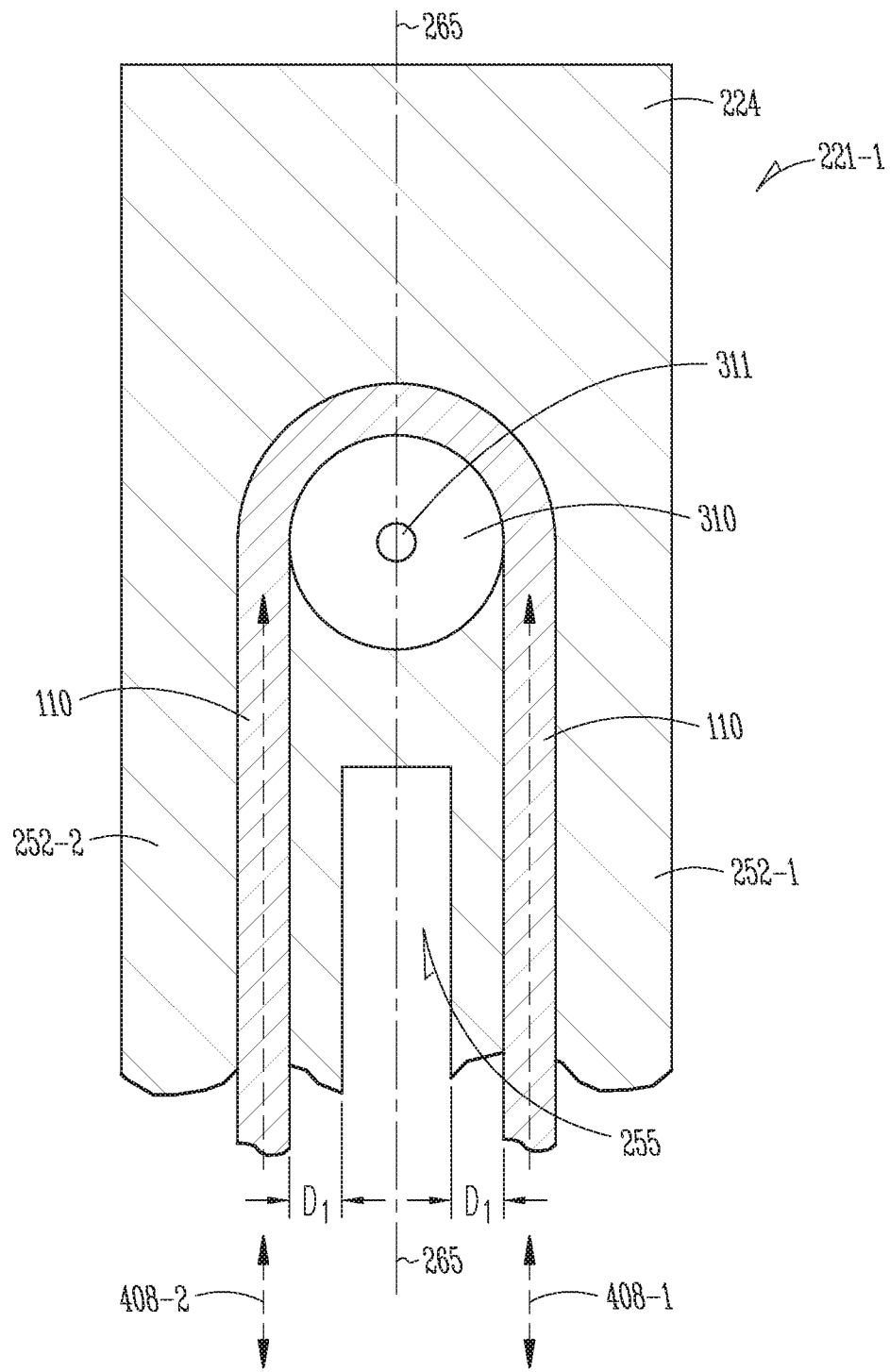
FIG. 13 is an illustrative top elevation view of the distal end portion of stapler cartridge support channel structure of a second jaw with the pair of coaxial distal end jaw mounted pulleys in accordance with some embodiments.

FIG. 11 is an illustrative perspective view of a distal end portion 221-1 of the stapler cartridge support channel structure 221 of the second jaw 216 with the pair of a coaxial distal end jaw mounted pulleys 310, 312, in accordance with some embodiments. FIG. 12 is an illustrative top perspective view of a proximal end portion 221-1 of the stapler cartridge support channel structure 221 of the second jaw 216, showing first and second pairs of coaxial proximal end jaw mounted pulleys 333, 343, in accordance with some embodiments. FIG. 13 is an illustrative top elevation view of the distal end portion 221-1 of the stapler cartridge support channel structure 221 of the second jaw 216 with the pair of coaxial distal end jaw mounted pulleys 310, 312 (only the top pulley visible), in accordance with some embodiments. To simplify the drawings of FIGS. 11-13 and to more clearly show the coaxial distal end pulleys 310, 312 the first and second pairs of coaxial proximal end pulleys 333, 343, and their relationship to the slider beam 104, the first jaw 214 and the stapler cartridge 218 are not shown.

Referring to FIGS. 10-12, the first and second channels 275, 277 and the first and second pulleys 310, 312 guide the first and pitch/slider cables 110, 112, vertically offset from one another by the vertical offset distance, between the first and second cantilever beams 274, 276 as they traverse the length of the jaw assembly 210. More specifically, the first pitch/slider cable segment 110 extends along a first lateral side of the second jaw 216 from the distal end of the second jaw 216 at a top-mounted guide pulley 330 of the first pair of coaxial proximal end jaw-mounted idler pulleys 333. The first pitch/slider cable 110 further extends through the first channel 275 and about the top distal end jaw mounted pulley 310. The first pitch/slider cable 110 further extends along a second lateral side of the second jaw 216 from the top mounted pulley 310 at the distal end of the second jaw 216-1 (also "second jaw distal end 216-1") to a top-mounted guide pulley 340 of the second pair of coaxial proximal end jaw-mounted idler pulleys 343. A crimp (not visible) in the first pitch/slider cable segment 110 engages the first crimp surface 402 that defines the crimp opening 281 such that a force applied along a longitudinal axis of the first pitch/slider cable 110 also is imparted to the slider beam 104.

Similarly, the second pitch/slider cable 112 extends along the first lateral side of the second jaw 216 from the distal end of the second jaw 216 at a bottom-mounted guide pulley 332 of the first pair of coaxial proximal end jaw-mounted guide pulleys 333. The second pitch/slider cable segment 112 further extends about the bottom distal end jaw mounted pulley 312. The second pitch/slider cable 112 further extends along the second lateral side of the second jaw 216 from the bottom mounted pulley 312 at the distal end of the second jaw 216-1, through the second channel 276, and to the bottom-mounted guide pulley 342 of the second pair of coaxial proximal end jaw-mounted guide pulleys 343. A crimp 406 in the second pitch/slider cable segment 112 engages the second crimp surface 404 that defines the crimp opening 282 such that a force applied along a longitudinal axis of the second pitch/slider cable 112 also is imparted to the slider beam 104.

In an alternative embodiment (not shown), the first top and bottom guide pulleys 340, 342 are disposed closer to the second top and bottom guide pulleys 340, 342 such their crimps and attachments are disposed on the same side of the slider beam 104.

More particularly, as best shown in FIG. 11, the first (top) and second (bottom) jaw-mounted coaxial distal mounted pulleys 310, 312 are shown mounted at a distal end 221-1 of the cartridge support structure 221 portion of the second jaw 216. The jaw-mounted coaxial first and second distal pulleys 310, 312 rotate about common axis 311-1. The first pitch/slider cable segment 110 wraps about the first distal pulley 310. The second pitch/slider cable segment 112 wraps around the second distal pulley 312. The distal end 221-1 of the cartridge support structure 221 includes the bottom wall 224 and opposed longitudinally extending sidewalls 225 that upstand from elongated edges thereof.

Referring to FIG. 13, the second elongated slot 255 is sized to receive the cross-beam portion 258 of the slider beam 104 and to guide it along the longitudinal length of the bottom wall 224 of the cartridge support structure 221. Arrows for first and second paths 408-1, 408-2 indicate the paths of movement of the first and second pitch/slider cable segments 110, 112 along the first and second sides of the second elongated slot 255. The second cable segment 112 is hidden behind the first cable segment 110 in this view. The first (top) distal pulley 310 is shown mounted on distal axle 311. The second (bottom) distal pulley 312 is hidden behind the first pulley 310 in this view. The shared axle 311 of the distal coaxial pulleys 310, 312 is aligned with a center axis 265 of the second elongated slot 255. The portions of the first and second pitch/slider cables 110, 112 extending along the opposite sides of the elongated second slot 255 are equally spaced from it by an amount $D_1$. Portions of the first and second cables 110, 112 extend above a first side edge 252-1 of the bottom wall 224 of the support structure 221, and portions of the first and second cables 110, 112 extend over a second side edge 252-2 of the bottom wall 224 of the support structure 221.

Slider Beam Jaw Clamping

Figure 14:
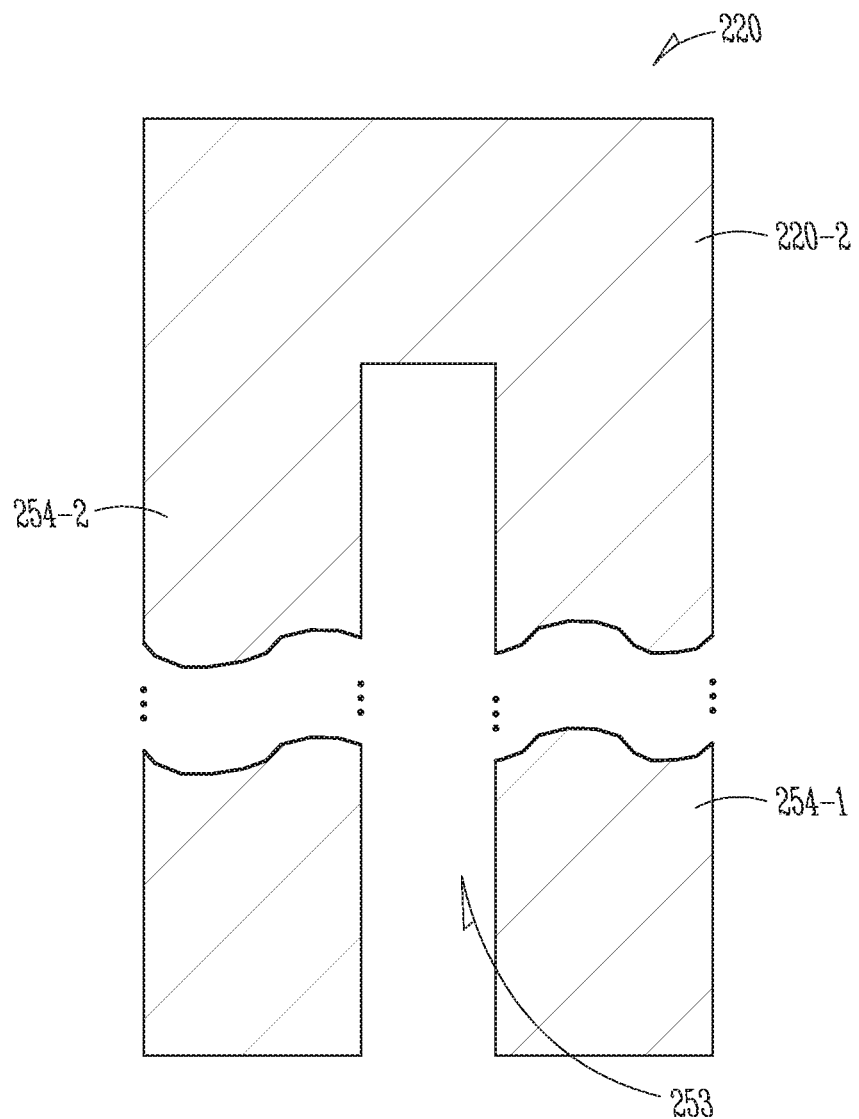
FIG. 14 is an illustrative top elevation view of the top surface of an anvil portion of the of a first jaw defining elongated first slot in accordance with some embodiments.

FIG. 14 is an illustrative top elevation view of the top (outer) surface of the anvil 220 portion of the of the first jaw 214 defining the elongated first slot 253, in accordance with some embodiments. A portion of an second (outer) surface 220-2 of the anvil 220, which faces away from the second jaw 216, includes a first parallel side edges 254-1, 254-2 that act as jaw clamping cam surfaces on opposite sides of the first elongated slot 253. The first jaw clamping cam surface 252 extends longitudinally along the first jaw 214. Referring again to FIGS. 11-13, an outward facing side of the bottom wall 224 of the support channel structure, which faces away from the first jaw 214, includes a second parallel side edges 253-1, 253-2 (not shown) that act as jaw clamping cam surfaces on opposite sides of the second elongated slot 255. The cross-beam portion 258 of the slider beam 104 extends through the cartridge slot 238 and through the first and second elongated slots 253, 255. The first transverse beam portion 260 interacts with the first jaw clamping cam surfaces 254-1, 254-2, and the second transverse beam 262 interacts with the second jaw clamping cam surfaces (not shown) so as to cooperate with each other to apply a clamping force to clamp the first and second jaws 214, 216 in a substantially fixed closed position while the slider beam 104 moves within the slots 238, 253, 255 longitudinally in a distal direction within the jaw assembly 210.

The first and second pitch/slider cable segments 110, 112 cooperate to move the slider beam 104 longitudinally within the jaw assembly 210. Referring again to FIG. 8, in accordance with some embodiments, as the slider beam 104 moves longitudinally in a distal direction along the length of the jaw assembly with the first and second jaws 214, 216 in a closed position, it pushes the staple pusher 244 in front of it. The staple pusher 244 includes a distally mounted ramp structure that comprises cam wedge 246 that urges fasteners (staples) 242 out from fastener retention slots 240 into staple deforming cavities (not shown) formed within the first anvil surface 220-1 of the first jaw 214 so as to insert and fasten the staples to tissue (not shown) that disposed between the first and second jaws 214, 216. In some embodiments, the cross-beam portion 258 defines a knife edge 239 that trails behind the staple pusher 244 as it moves in a distal direction so as to cut tissue portions after they have been stapled. Thus, as the first and second pitch/slider cable segments 110, 112 move the slider beam 104 longitudinally along the length of the jaw assembly, the first and second first transverse beam portions 260, 262 urge towards one another the first and second jaws 214, 216, while the transverse portion 258 pushes the staple pusher 244 in front of causing fasteners 242 to be dispensed. U.S. Pat. No. 8,991,678 (filed Oct. 26, 2012) issued to Wellman et al., which is incorporated herein in its entirety by this reference, discloses a surgical stapler cartridge and its operation.

Pitch/Slider Cable Segment Engagement with Slider Beam

Referring again to FIG. 12, the first (top) proximal coaxial pulley 330 is coaxially mounted with a second (bottom) proximal coaxial pulley 332 of the first pair of proximal coaxial pulleys 333. The second pulley 332 is substantially hidden beneath the first pulley 330 shown in this view of the first pair 333. The first (top) proximal coaxial pulley 340 is coaxially mounted with the second (bottom) proximal coaxial pulley 342 of the second pair of pulleys 343. The second pulley 342 is substantially hidden beneath the first pulley 340 shown in this view of the second pair of pulleys 343.

The first and second pairs 333, 343 of coaxial proximally mounted pulleys are disposed between the two-degree-of-freedom (2dof) wrist 208 and the slider beam 104, which has its cross-beam portion 258 slidably inserted within the elongated slots 238, 253, 255. The respective first (top) proximal pulleys 330, 340 engage the first cable segment 110 and urge it to follow parallel paths on either side of the elongated slots 238, 253, 255. An inward-facing portion of the first (top) pulley 330 of the first pair 333 engages the first cable 110 and urges it inwardly to follow the first path 408-1 shown in FIG. 13, which is spaced by the amount $D_1$ from the second elongated slot 255. An inward-facing portion of the first (top) pulley 340 of the second pair of pulleys 343 also engages the first cable 110 and urges it inwardly to follow the second path 408-2 shown in FIG. 13, which is spaced by the amount $D_1$ from an opposite side of the second elongated slot 255. Thus, the first (top) pulleys 330, 340 of the first and second pairs 333, 343 of pulleys guide the first cable segment 110 in its movement along opposite sides of the second elongated slot 255.

Similarly, the respective second (bottom) proximal pulleys 332, 342 engage the second cable segment 112 and urge it to follow parallel paths on either side of the elongated slots 238, 253, 255. An inward-facing portion of the second (bottom) pulley 332 of the first pair 333 engages the second cable 112 and urges it inwardly to follow parallel to the first path 408-1 shown in FIG. 13 that is spaced by the amount $D_1$ from the second elongated slot 255. An inward-facing portion of the second (bottom) pulley 342 of the second pair of pulleys 343 also engages the second cable 112 and urges it inwardly to follow parallel to the second path 408-2 shown in FIG. 13, which is spaced by the amount $D_1$ from an opposite side of the second elongated slot 255. Thus, the second (bottom) pulleys 332, 342 of the first and second pairs 333, 343 of pulleys guide the second cable segment 112 in its movement along opposite sides of the second elongated slot 255.

Moreover, the top proximal pulleys 330, 332 cooperate to urge the first pitch/slider cable 110 inwardly toward the second elongated slot 255 and into slideably rotational engagement with outer surfaces of the first pitch axis pulley 450 such that longitudinal movement of the first pitch/slider cable 110 within the second jaw 216 imparts a rotational force to the first pitch axis pulley 450. Similarly, the bottom proximal pulleys 340, 342 cooperate to urge the second pitch/slider cable 112 inwardly toward the second elongated slot 255 and into slideably rotational engagement with outer surfaces of the second pitch axis pulley 452 such that longitudinal movement of the second pitch/slider cable 112 within the second jaw 216 imparts a rotational force to the second pitch axis pulley 452. As explained with reference to FIGS. 17A-17D, direction of longitudinal motion of the first and second pitch/slider cables 110, 112 determines directions of rotational forces imparted by the cables 110, 112 to the first and second pitch pulleys 450, 452.

Thus, the portion of the first pitch/slider cable 110 that travels along the first path 408-1 includes a crimp (not shown) that secures it to the first cantilever beam channel 275 such that the beam travels in-line with the first cable 110 as it moves along the first path 408-1. The portion of the first cable segment 110 that travels along the second path 408-2 passes above the second cantilever beam 276. Also, the second cable segment 112 that travels along the second path 408-2 includes the crimp 406 that secures it to the second cantilever beam channel 277 such that the beam travels in-line with the second cable 112 as it moves along the second path 408-2. The portion of the second cable segment 112 that travels along the first path 408-1 passes below the first cantilever beam 274.

Overview of 2-DOF Wrist Cables and Pulleys and Attachment to Second Jaw

Figure 15:
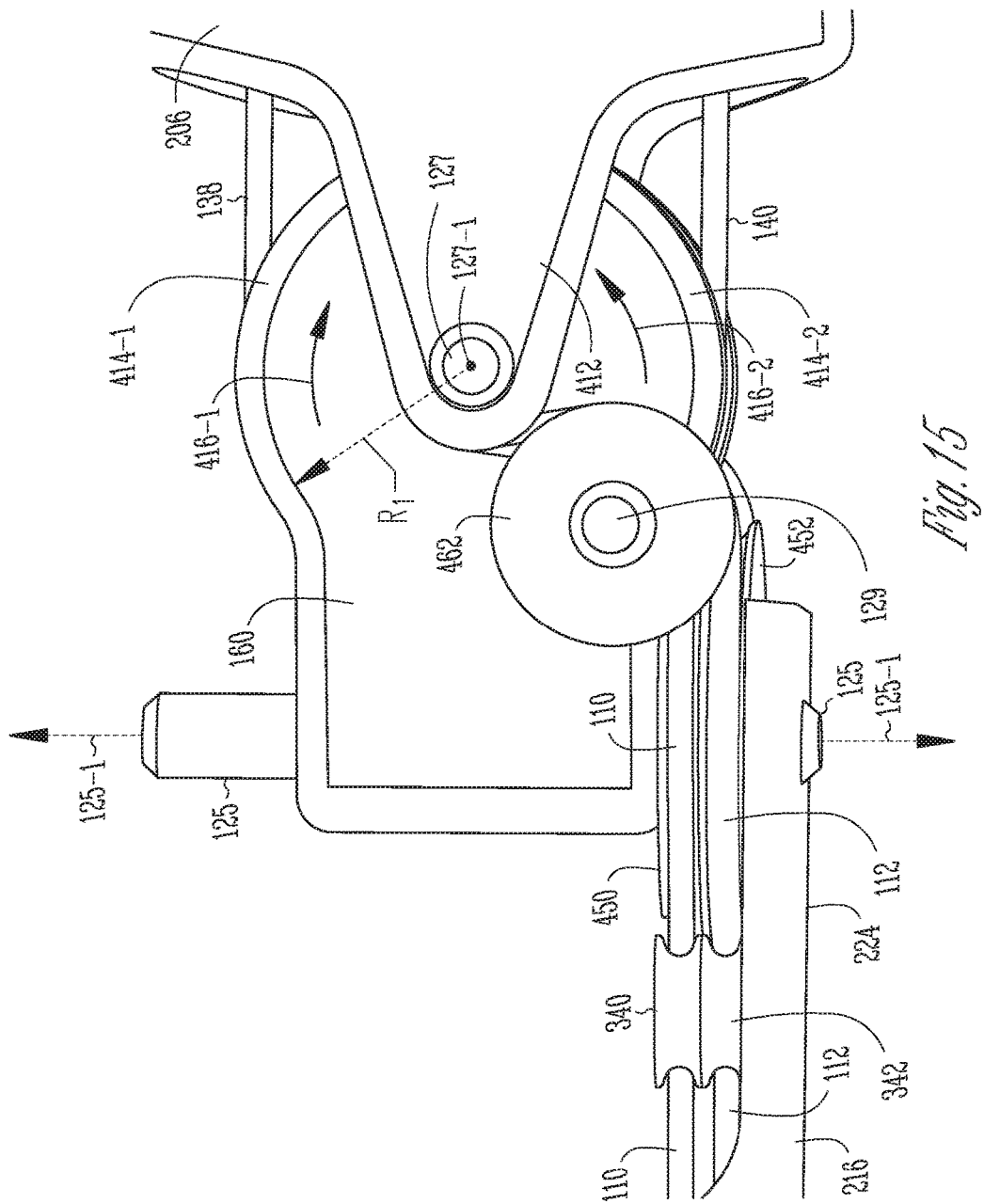
FIG. 15 is an illustrative side view of a two degree of freedom wrist in accordance with some embodiments.

FIG. 15 is an illustrative side view of a two degree of freedom wrist 208 in accordance with some embodiments. A dual axis support member 160 defines a first bore (not shown) having a bearing surface (not visible) to support a pitch axle 125 aligned with a pitch axis 125-1 and defines a second bore (not shown) having a bearing surface (not visible) to support a yaw axle 127 aligned with a yaw axis 127-1. The pitch axis 125-1 and the yaw axis 127-1 are perpendicular to one another. The dual axis support member 160 also includes a pair of pivot axles 129 (only one visible) that extend parallel to the yaw axle 127 from opposite sides of the support member 160. In some embodiments, the pivot axles 129 are disposed to act as yaw rotation pivot points during yaw direction movement of the wrist 208. The pivot axles 129 are operatively disposed between the yaw axle 127 and the second jaw 216. A proximal end of the bottom wall 224 of second jaw 216 defines a bore (not shown) into which one end of the pitch axle 125 extends and in which the pitch axle 125 is rotatably secured. Thus, the pitch axle 125 acts to rotatably secure the jaw assembly 210 to the 2dof wrist 208.

Yaw Cable Routing Mechanism

Yaw cable routing is described with reference to FIG. 12 and FIG. 15. A distal end portion of the main shaft 206 and the yaw axle 127 are configured to act as a clevis 410 that mounts the wrist 208 and the jaw assembly 210, which depends therefrom for rotation about the yaw axis 127-1. More particularly, a proximal end of the main shaft 206 includes opposed support arms 412 that define bores (not shown) aligned to receive opposite ends of the yaw axle 127. The dual axis support member 160 is mounted on the yaw axle 127 between the support arms 412 for rotation about the yaw axis 127-1. Moreover, the dual axle support member 160 defines a yaw pulley 414 rotatably mounted to the yaw axle 127 and having a radius $R_1$. A first yaw cable segment 138 extends from within the main shaft 206 to an upper first portion 414-1 of the yaw pulley 414, and a second yaw cable segment 140 extends from within the main shaft 206 to an opposite lower second portion 414-2 of the yaw pulley 414. The first and second portions of the yaw pulley are substantially diametrically opposite one another. The first yaw cable segment 138 is secured to the first portion 414-1 of the yaw pulley 414 such that a force pulling in a distal direction upon the first yaw cable segment 138 causes the entire dual axis support member 160 to rotate in a clockwise direction as indicated by arrow 416-1. The second yaw cable segment 140 is secured to the second portion 414-2 of the yaw pulley 414 such that a force pulling in a distal direction upon the second yaw cable segment 140 causes the entire dual axis support member 160 to rotate in a counter-clockwise direction as indicated by arrow 416-2.

Pitch/Slider Cable Routing Mechanism

Pitch/slider cable routing is described with reference to FIGS. 11-12 and FIG. 15. The first (pitch/slider) cable segment 110 and the second pitch/slider segment 112 cooperate to achieve both pitch motion of the wrist 208 and also, to achieve longitudinal motion of the slider beam 104 along the jaw assembly 210. As explained above, the first pitch/slider cable segment 110 is routed about the jaw-mounted first distal pulley 310, and engages the first (top) pulleys 330, 340 of the first and second pulley pairs 333, 343. In addition, the first pitch/slider cable segment 110 engages a first pitch axis pulley 450 mounted to rotate about the pitch axle 125, engages each one of a pair of first pivot point pulleys 460 (only one visible) mounted on the pivot axles 129 on opposite sides of the support member 160, and engages each one of a first pair of yaw axis pulleys 470 (only one visible) mounted on the yaw axle 127 on opposite sides of the support member 160. The first pitch axis pulley 450, the first pivot point pulleys 460, and the first yaw axis pulleys 470 are aligned with each other to provide a substantially straight longitudinal line path for the first pitch/slider cable 110 to follow between a vertical elevation of the yaw axle 127 and a vertical elevation of the first (top) pulleys 330, 340 of the first and second pulley pairs 333, 343, operable over approximately plus or minus seventy degrees of yaw range of motion.

Similarly, as explained above, the second pitch/slider cable segment 112 is routed about the jaw-mounted second distal pulley 312, and engages the second (bottom) pulleys 332, 342 of the first and second pulley pairs 333, 343. In addition, the second pitch/slider cable segment 112 engages a second pitch axis pulley 452, which is mounted coaxially with the first pitch axis pulley 450, to rotate about the pitch axle 125, engages each one of a pair of second pivot point pulleys 462, which are mounted on opposite sides of the support member 160 coaxially with and outboard of the first pivot point pulleys 460. The second pitch/slider cable segment 112 also engages each one of a second pair of yaw axis pulleys 472, which are mounted on opposite sides of the support member 160 coaxially with and outboard of the first yaw axis pulleys 470 mounted on the yaw axle 127 on opposite sides of the support member 160. The second pitch axis pulley 452, the second pivot point pulleys 462, and the second yaw axis pulleys 472 are aligned with each other to provide a substantially straight longitudinal line path for the second pitch/slider cable 112 to follow between a vertical elevation of the yaw axle 127 and a vertical elevation of the second (bottom) pulleys 332, 342 of the first and second pulley pairs 333, 343. More specifically the first pitch axis pulley 450 is vertically aligned with the first (top) pulleys 330, 340 of the first and second pulley pairs 333, 343. The second pitch axis pulley 452 is vertically aligned with the second (bottom) pulleys 332, 342 of the first and second pulley pairs 333, 343. The first pitch axis pulley 450 has a smaller diameter than the second pitch axis pulley 452. The first pivot point pulleys 460 are sized and oppositely positioned to have outer diameters that align with opposite portions first pitch axis pulley 450. The second pivot point pulleys 462 are sized and oppositely positioned to have outer diameters that align with opposite portions of the second pitch axle 452. The first and second pairs of yaw axis pulleys, 470, 472 have matching diameters that are smaller than a diameter of the yaw pulley 414 so as to minimize forces imparted to the yaw pulley 414 due to rotation imparted the first and/or second pairs of yaw axis pulleys, 470, 472 in response to motion of the first and/or second pitch/slider cable segments 110, 112.

Figure 16:
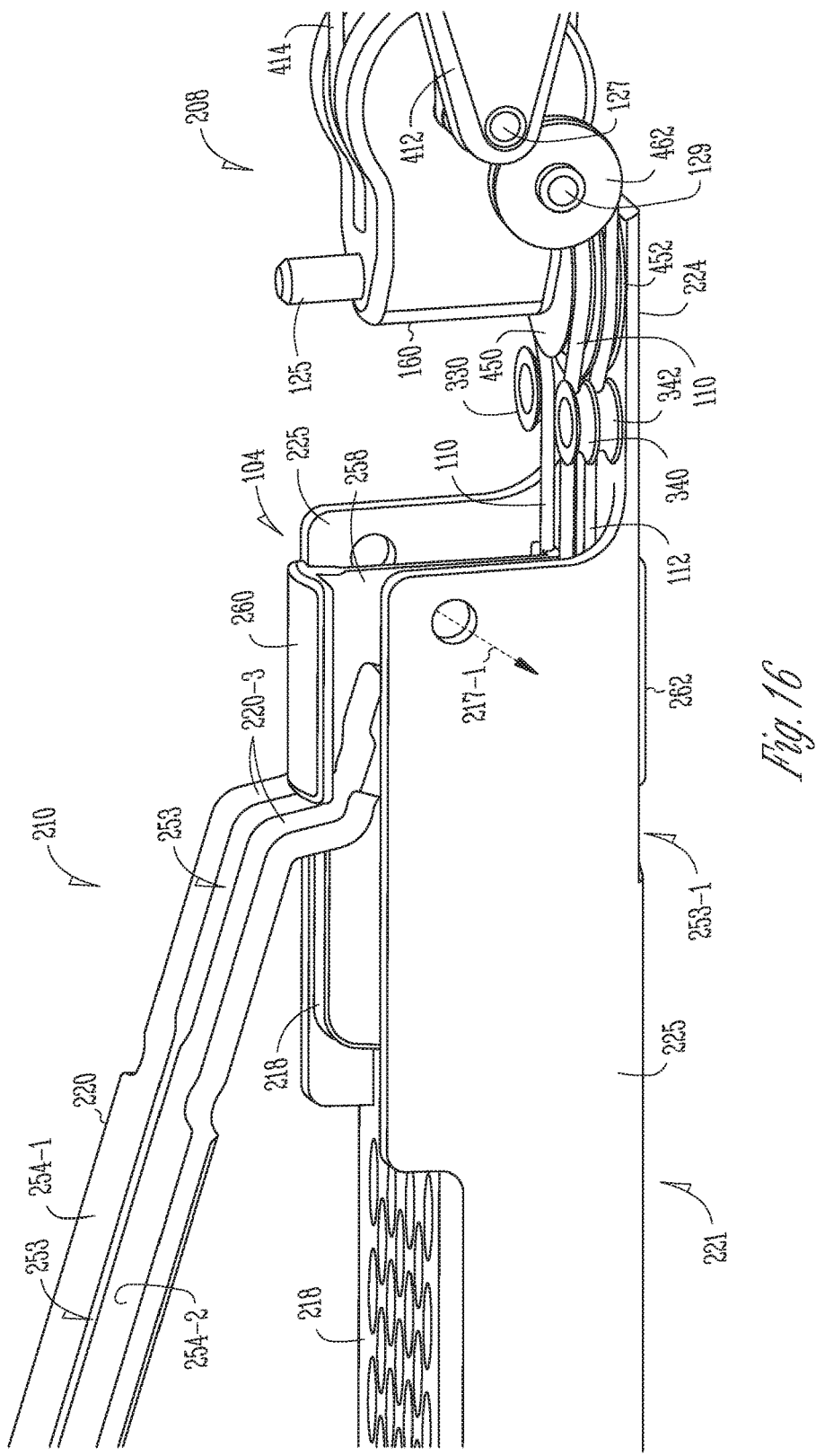
FIG. 16 is a perspective side elevation partial view of a proximal end portion of the jaw assembly and a wrist with the jaw assembly in an open position, in accordance with some embodiments.

FIG. 16 is a perspective side elevation partial view of a proximal end portion of the jaw assembly 210 and the wrist 208 with the jaw assembly 210 in an open position, in accordance with some embodiments. Certain components are omitted from the drawings in FIG. 16 in order to not obscure other features and so as to simplify the explanation. A proximal portion of the anvil 220 includes inclined cam edges 220-3 that extend along opposite sides of a proximal portion of the first elongated longitudinal slot 253. As the slider beam 104 starts its motion from a proximal position within the jaw assembly 210 and moves toward a distal position within the jaw assembly 210, a distal edge of the first transverse beam portion 260 engages the inclined cam edges 220-3 causing the anvil 220 of the first jaw 214 to rotate about the jaw rotation axis 217-1 toward the cartridge support channel structure 221 of the second jaw 216, which in turn, so as to configure the jaw assembly 210 in a closed position in which the cross-beam portion extends through the slots 238, 253 and 255, and the first transverse beam portion 260 and the second transverse beam portion 262 exert a clamping force upon the first and second jaws 214, 216 holding them together as it traverses in a distal direction within the jaw assembly 210.

It will be understood that in some embodiments, the first pitch/slider cable segment 110 comprises a single integral cable segment that extends between the first pair of yaw axis pulleys 470. Alternatively, the first pitch/slider cable segment 110 may comprise separate integral cable segments. Likewise, in some embodiments, the second pitch/slider cable segment 112 comprises a single integral cable segment that extends between the second pair of yaw axis pulleys 472. Alternatively, the first pitch/slider cable segment 112 may comprise separate integral cable segments.

Forces and Motion Imparted by Pitch/Slider Cables

FIGS. 17A-17D are illustrative drawings representing functional relationships between different forces imparted to the first and second pitch/slider cable segments 110, 112 and motion imparted to the slider beam 104 and to the first and second pitch pulleys 450, 452 by motors (not shown) within the proximal actuation assembly 202, in accordance with some embodiments. For illustrative purposes, the first and second pitch/sliders 110, 112 are shown laterally spaced apart, although in the present embodiment they are vertically aligned one directly above the other. Moreover, for illustrative purposes and simplifying the explanation, the paths of the first and second pitch/sliders 110, 112 are shown but the pulleys such as pulleys 310, 312, 450, 452, for example, that guide them along these paths are not shown. As described above, the first pitch/slider cable 110 is secured at a first crimp surface 402 to the first cantilever beam 274 and wraps about opposed outer perimeter portions of the first (top) distal jaw-mounted pulley 310 and the first pitch axis pulley 450. The second pitch/slider cable 112 is secured at a second crimp surface 404 to the second cantilever beams 276 and wraps about opposed outer perimeter portions of the (bottom) distal jaw-mounted pulley 312 and the second pitch axis pulley 452. Motors (not shown) disposed within the proximal actuation assembly 202 or the patient side cart 22 exert controllable tension forces upon the pitch/slider cables to cause the left side of the first pitch/slider cable 110 to move opposite the right side of the first pitch/slider cable 110 and to cause the left side of the second pitch/slider cable 112 to move opposite the right side of the second pitch/slider cable 112, such that for each cable, a portion on one side of the distal jaw-mounted pulleys 310, 312 is retracted in a proximal direction to within the bore within the main shaft 206 while another portion of the same cable on the other side of the distal jaw-mounted pulleys 310, 312 is drawn out in a distal direction from within the bore within the main shaft 206. As the first pitch/slider cable 110 moves longitudinally along the second jaw 220 in either a proximal direction or a distal direction, a proximal portion of the first pitch/slider cable 110 imparts a clockwise or counter-clockwise rotational first upon the first pitch axis pulley 450. Similarly, as the second pitch/slider cable 112 moves longitudinally along the second jaw 220 in either a proximal direction or a distal direction, a proximal portion of the second pitch/slider cable 112 imparts a clockwise or counter-clockwise rotational forces upon the second pitch axis pulley 452. All references to "clockwise" or "counter-clockwise" are relative to the plane of the page on which the figure is shown.

Figure 17A:
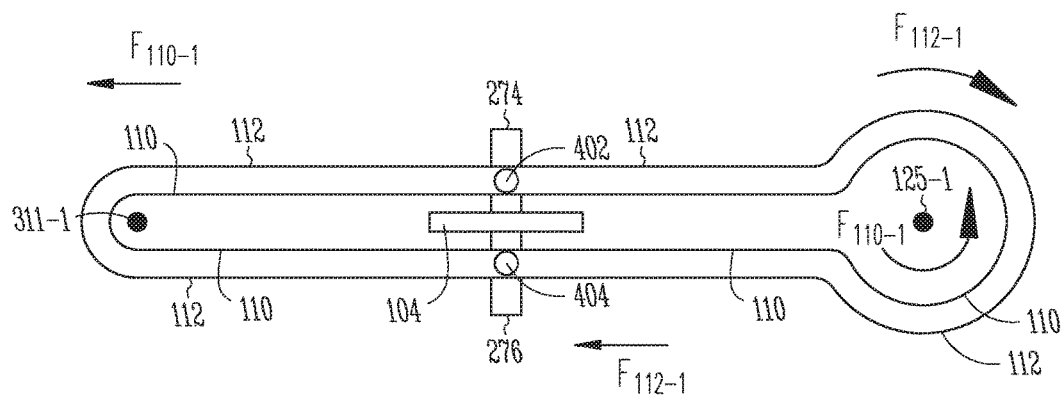
FIGS. 17A-17D are illustrative drawings representing functional relationships between different forces exerted by first and second pitch/slider cable segments and resultant motion imparted to a slider beam and to a wrist in accordance with some embodiments.

FIG. 17A is an illustrative drawing indicating a first direction force $F_{110-1}$ imparted by a motor (no shown) upon the first pitch/slider cable 110 while a first direction force $F_{112-1}$ imparted by a motor (not shown) upon the second pitch/slider cable 112 in accordance with some embodiments. The first direction force $F_{110-1}$ imparted to the first pitch/slider cable 110 imparts a distal direction force upon the pitch/slider beam 104 and imparts a counter-clockwise rotation force upon the first pitch axis pulley 450. The first direction force $F_{112-1}$ imparted to the second pitch/slider cable 112 imparts a distal direction force upon the slider beam 104 and exerts a clockwise rotation force upon the second pitch axis pulley 452. A result of the simultaneous exertion of the first direction forces $F_{110-1}$, $F_{112-1}$ upon the first and second pitch/slider cable segments 110, 112 is distal direction movement of the slider beam 104 and stationary (i.e. no motion) position of the first and second pitch axis pulleys 450, 452, which results in the wrist 208 being stationary. The opposed rotation forces imparted by the first and second slider/pitch cables 110, 112 to the first and second pitch pulleys 450, 452 as they slide across the pitch pulley outer surfaces cancel each other resulting no rotation of the first and second pitch pulleys 450, 452 about the pitch axis and no rotation of the wrist 208.

Figure 17B:
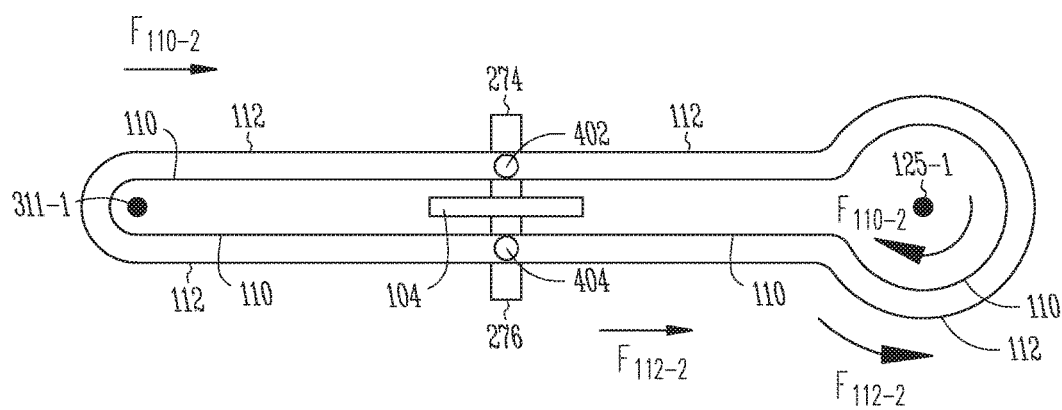

FIG. 17B is an illustrative drawing indicating a second direction force $F_{110-2}$ imparted by a motor (no shown) upon the first pitch/slider cable 110 while a second direction force $F_{112-2}$ imparted by a motor (not shown) upon the second pitch/slider cable 112 in accordance with some embodiments. The second direction force $F_{110-2}$ imparted to the first pitch/slider cable 110 imparts a proximal direction force upon the slider beam 104 and imparts a clockwise rotation force upon the first pitch axis pulley 450. The second direction force $F_{112-2}$ imparted to the second pitch/slider cable 112 imparts a proximal direction force upon the slider beam 104 and imparts a counter-clockwise rotation force upon the second pitch axis pulley 452. A result of the simultaneous exertion of the second direction forces $F_{110-2}$, $F_{112-2}$ upon the first and second cable segments 110, 112 is proximal direction movement of the slider beam 104 and stationary (i.e. no motion) position of the first and second pitch axis pulleys 450, 452, which results in the wrist 208 being stationary. The opposed rotation forces imparted by the first and second slider/pitch cables 110, 112 to the first and second pitch pulleys 450, 452 as they slide across the pitch pulley outer surfaces cancel each other resulting no rotation of the first and second pitch pulleys 450, 452 about the pitch axis and no rotation of the wrist 208.

Figure 17C:
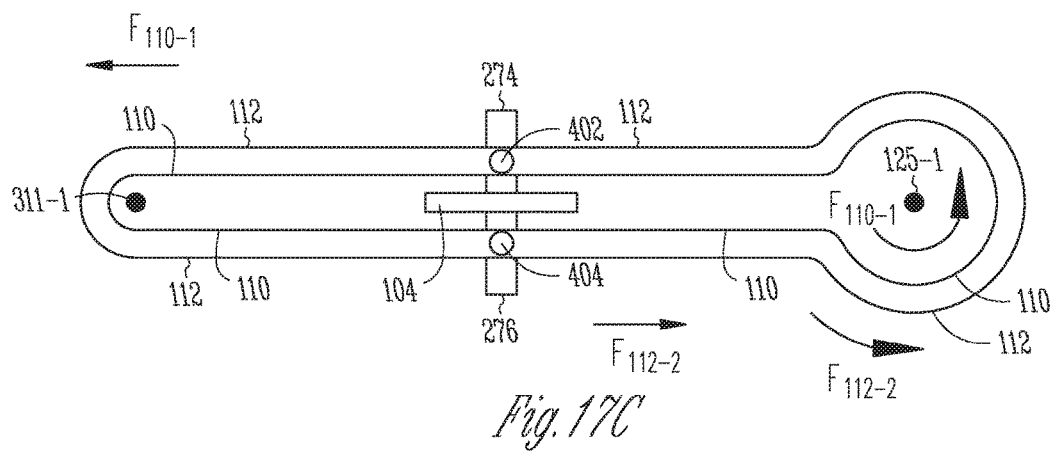

FIG. 17C is an illustrative drawing indicating the first direction force $F_{110-1}$ imparted by a motor (not shown) upon the first pitch/slider cable 110 while the second direction force $F_{112-2}$ is imparted by a motor (not shown) upon the second pitch/slider cable 112 in accordance with some embodiments. The first direction force $F_{110-1}$ imparted to the first pitch/slider cable 110 imparts a distal direction force upon the slider beam 104 and imparts a counter-clockwise rotation force upon the first pitch axis pulley 450. The second direction force $F_{112-2}$ imparted upon the second pitch/slider cable 112 exerts a proximal direction force upon the slider beam 104 and imparts a counter-clockwise rotation force upon the second pitch axis pulley 452. Furthermore, the first direction force $F_{110-1}$ and the second direction force $F_{112-2}$ apply a counter-clockwise moment to slider beam 104, locking slider beam 104 relative to the jaws of the device. A result of the simultaneous exertion of the first direction force $F_{110-1}$ and the second direction force $F_{112-2}$ upon the first and second cable segments 110, 112, respectively, is stationary (i.e. no motion) position of the slider beam 104 and counter-clockwise direction pitch rotation of the first and second pitch pulleys 450, 452, which results in counter-clockwise pitch rotation of the wrist 208. The opposed longitudinal forces imparted by the first and second slider/pitch cables 110, 112 to the slider beam 104 as they slide across the pitch pulley outer surfaces cancel each other resulting in stationary (i.e. no motion) longitudinal position of the slider beam 104 and counter-clockwise pitch rotation of the first and second pitch pulleys 450, 452 about the pitch axis, which causes counter-clockwise pitch rotation of the wrist 208.

Figure 17D:
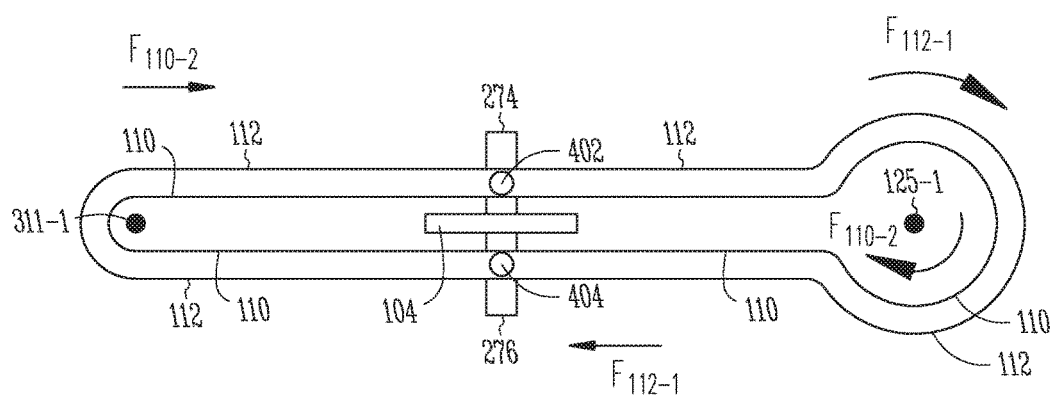

FIG. 17D is an illustrative drawing indicating the second direction force $F_{110-2}$ imparted by a motor (not shown) upon the first pitch/slider cable 110 while the first direction force $F_{112-1}$ is imparted by a motor (not shown) upon the second pitch/slider cable 112 in accordance with some embodiments. The second direction force $F_{110-2}$ imparted upon the first pitch/slider cable 110 imparts a proximal direction force upon the slider beam 104 and imparts a clockwise rotation force upon the first pitch axis pulley 450. The first direction force $F_{112-1}$ imparted upon the second pitch/slider cable 112 imparts a distal direction force upon the slider beam 104 and imparts a clockwise rotation force upon the second pitch pulley 452. Furthermore, the second direction force $F_{110-2}$ and the first direction force $F_{112-1}$ apply a clockwise moment to slider beam 104, locking slider beam 104 relative to the jaws of the device. A result of the simultaneous exertion of the second direction force $F_{110-2}$, and the first direction force $F_{112-1}$ upon the respective first and second cable segments 110, 112, respectively, is stationary (i.e. no motion) longitudinal position of the slider beam 104 and clockwise direction pitch rotation of the first and second pitch pulleys 450, 452, which results in clockwise rotation of the wrist 208. The opposed longitudinal forces imparted by the first and second slider/pitch cables 110, 112 to the slider beam 104 as they slide across the pitch pulley outer surfaces cancel each other resulting in stationary (i.e. no motion) longitudinal position of the slider beam 104 and clockwise pitch rotation of the first and second pitch pulleys 450, 452 about the pitch axis, which causes clockwise pitch rotation of the wrist 208.

Forces and Motion Imparted by Yaw Cables

One or more motors (not shown) disposed within the proximal actuation assembly 202 or within the patient side cart 22 exert controllable tension forces upon the yaw cable segments 138, 140 to impart yaw motion to the 2dof wrist 208. Referring again to FIG. 15, a proximal direction force exerted upon the first yaw cable segment 138, while a lesser proximal direction tensioning force is exerted upon force upon the second yaw cable segment 140 results in clockwise yaw direction motion of the dual axis support member 160, which is indicated by arrow 416-1. Conversely, a proximal direction force exerted upon the second yaw cable segment 140, while a lesser proximal direction tensioning force is exerted upon force upon the first yaw cable segment 138 results in counter-clockwise yaw direction motion of the dual axis support member 160, which is indicated by arrow 416-2.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. A medical device, comprising:
   an elongate shaft having a proximal end, a distal end, and a longitudinal axis extending between the proximal end and the distal end;
   a jaw coupled to the distal end of the elongate shaft, the jaw being configured to rotate relative to the longitudinal axis of the elongate shaft about a pitch axis, the jaw having a proximal end, a distal end, and a longitudinal axis extending between the proximal end and the distal end;
   a first distal pulley and a second distal pulley rotatably coupled to the jaw towards the distal end of the jaw;
   a slider beam movably coupled to the jaw, the slider beam including a cross-beam portion that extends along a median plane of the slider beam;
   a first cable coupled to the slider beam at a first lateral distance from the median plane of the slider beam on a first side of the median plane, the first cable including a first segment that extends distally from the slider beam and a second segment that extends proximally from the slider beam, wherein the first segment of the first cable wraps around the first distal pulley and then extends towards the proximal end of the jaw; and
   a second cable coupled to the slider beam at a second lateral distance from the median plane of the slider beam on a second side of the median plane, the second cable including a first segment that extends distally from the slider beam and a second segment that extends proximally from the slider beam, wherein the first segment of the second cable wraps around the second distal pulley and then extends towards the proximal end of the jaw.

2. The medical device of claim 1, wherein the first lateral distance is equal to the second lateral distance.

3. The medical device of claim 1, wherein the first distal pulley and the second distal pulley rotate about a common axis.

4. The medical device of claim 1, wherein a radius of the first distal pulley is equal to the first lateral distance, and a radius of the second distal pulley is equal to the second lateral distance.

5. The medical device of claim 1, wherein increasing the tension in the first segment of the first cable and the first segment of the second cable moves the slider beam towards the distal end of the jaw.

6. The medical device of claim 1, wherein increasing the tension in the second segment of the first cable and the second segment of the second cable moves the slider beam towards the proximal end of the jaw.

7. The medical device of claim 1, wherein increasing the tension in the first segment of the first cable and the second segment of the second cable maintains the position of the slider beam relative to the jaw and rotates the jaw relative to longitudinal axis of the elongate shaft in a first direction.

8. The medical device of claim 1, wherein increasing the tension in the second segment of the first cable and the first segment of the second cable maintains the position of the slider beam relative to the jaw and rotates the jaw relative to the longitudinal axis of the elongate shaft in a second direction.

9. A surgical instrument comprising:
   a jaw assembly that includes first a first jaw that defines a first elongated slot and a second jaw that defines a second elongated slot, each jaw each having a proximal end and a distal end, wherein the proximal ends of the first and second jaws are coupled to one another for rotational motion of the distal ends of the first and second jaws between an open position and a closed position;
   a slider beam that includes a cross-beam portion slidably mounted within the first and second slots;
   first and second distal jaw-mounted coaxial pulleys rotatably mounted to a distal portion of the second jaw;
   a two degree of freedom wrist that includes first and second pitch axis pulleys rotatable about a pitch axis and that includes a yaw pulley rotatable about a yaw axis;
   a first pitch/slider cable that is secured to the cross-beam portion of the slider beam, that wraps about the first distal jaw-mounted pulley and that extends parallel to the first and second elongated slots to slideably engage opposite sides of the first pitch axis pulley;
   a second pitch/slider cable that is secured to the cross-beam portion of the slider beam, that wraps about the second distal jaw-mounted pulley and that extends parallel to the first and second elongated slots to slideably engage opposite sides of the second pitch axis pulley; and
   at least one yaw cable wrapped about at least a portion of the yaw pulley.

10. The surgical instrument of claim 9,
    wherein the first pitch/slider cable extends along opposite sides of the first and second elongated slots; and
    wherein the second pitch/slider cable extends along opposite sides of the first and second elongated slots.

11. The surgical instrument of claim 9,
    wherein the cross-beam portion includes opposite facing first and second side faces;
    wherein the first pitch/slider cable extends along opposite sides of the first and second elongated slots and is secured to a portion of the first side face; and
    wherein the second pitch/slider cable extends along opposite sides of the first and second elongated slots and is secured to a portion of the second side face.

12. The surgical instrument of claim 9 further including:
a pair of first coaxial guide pulleys rotatably mounted to a proximal portion of the second jaw between the slider beam and the first and second elongated slots and configured for rotation parallel to the pitch axis;
a pair of second coaxial guide pulleys rotatably mounted to a proximal portion of the second jaw between the slider beam and the first and second elongated slots and configured for rotation parallel to the pitch axis;
wherein one of the pair of first guide pulleys and one of the pair of second guide pulleys are disposed to engage the first pitch/slider cable and to urge the first pitch/slider cable to engage opposite sides of the first pitch axis pulley; and
wherein another of the pair of first guide pulleys and another of the pair of second guide pulleys are disposed to engage the second pitch/slider cable and to urge the second pitch/slider cable to engage opposite sides of the second pitch axis pulley.

13. The surgical instrument of claim 9 further including:
a motor system configured to selectively impart force to the first pitch/slider cable in a proximal direction or in a distal direction and to selectively impart force to the second pitch/slider cable in a proximal direction or in a distal direction.

14. The surgical instrument of claim 9 further including:
a motor system configured to selectively impart force to the first pitch/slider cable in a proximal direction or in a distal direction and to selectively impart force to the second pitch/slider cable in a proximal direction or in a distal direction;
wherein the first and second pitch/slider cables are secured to the cross-beam portion such that,
  forces imparted by the motor system in opposite directions on the first and second pitch/slider cables cause the first and second pitch axis pulleys to rotate in the same directions causing the wrist to rotate about the pitch axis and cause the cross-beam portion to remain at a stationary longitudinal position within the jaw assembly; and
  forces imparted by the motor system in same directions on the first and second pitch/slider cables cause the first and second pitch axis pulleys to remain at a stationary rotational positions about the pitch axis causing the wrist to remain at a stationary rotational position about the pitch axis and cause the cross-beam portion to move longitudinally within the jaw assembly.

15. The surgical instrument of claim 9,
wherein the cross-beam portion includes opposite facing first and second side faces; further including:
a first cantilever beam that extends laterally outward from the first side face and that defines a first channel;
a second cantilever beam that extends laterally outward from the second side face and that defines a second channel;
wherein the first pitch/slider cable extends through the first channel; and
wherein the second pitch/slider cable extends through the second channel.

16. The surgical instrument of claim 9,
wherein the first jaw includes first parallel side edges that extend parallel to a longitudinal first axis of the first jaw and define the first elongated slot between them;
wherein the second jaw includes second parallel side edges that extend parallel to a longitudinal second axis of the second jaw and define the second elongated slot between them; and
wherein the slider beam includes a first transverse beam configured to slideably engage surfaces of the first parallel side edges facing away from the second jaw, and includes a second transverse beam configured to slideably engage surfaces of the second parallel side edges facing away from the first jaw.

17. The surgical instrument of claim 9,
wherein the two degree of freedom wrist further includes a first pitch/slider cable routing mechanism that includes at least two pulleys disposed to route the first pitch/slider cable between the yaw axis and first and second sides of the first pitch axis pulley; and
wherein the two degree of freedom wrist further includes a second pitch/slider cable routing mechanism that includes at least two pulleys disposed to route the second pitch/slider cable between the yaw axis and first and second sides of the first pitch axis pulley.

18. The surgical instrument of claim 9,
wherein the two degree of freedom wrist further includes a pitch/slider cable routing mechanism that includes:
at least two first inner pulleys disposed on a first side of the yaw pulley, wherein at least one of the first inner pulleys is mounted coaxially with the yaw pulley and the at least two first inner pulleys are aligned with each other to guide a portion of the first pitch/slider cable vertically between a yaw axis and a first side of the first pitch axis pulley;
at least two second inner pulleys disposed on a second side of the yaw pulley, wherein at least one of the second inner pulleys is mounted coaxially with the yaw pulley and the at least two second inner pulleys are aligned with each other to guide a portion of the first pitch/slider cable vertically between the yaw axis and a second side of the first pitch axis pulley;
at least two first outer pulleys disposed on the first side of the yaw pulley, wherein at least one of the first outer pulleys is mounted coaxially with the yaw pulley, outboard of the first inner pulley mounted coaxially with the yaw pulley, and the at least two first outer pulleys are aligned with each other to guide a portion of the second pitch/slider cable vertically between the yaw axis and a first side of the second pitch axis pulley; and
at least two second outer pulleys disposed on the second side of the yaw pulley, wherein at least one of the second outer pulleys is mounted coaxially with the yaw pulley, outboard of the second inner pulley mounted coaxially with the yaw pulley, and the at least two second outer pulleys are aligned with each other to guide a portion of the second pitch/slider cable vertically between the yaw axis and a second side of the second pitch axis pulley.

19. The surgical instrument of claim 18,
wherein the at least two first inner pulleys are aligned to provide a substantially straight longitudinal line path for a portion of the first pitch/slider cable to follow between the first inner pulley and the first side of the first pitch axis pulley;
wherein the at least two second inner pulleys are aligned to provide a substantially straight longitudinal line path for a portion of the first pitch/slider cable to follow between the second inner pulley and the second side of the first pitch axis pulley;

wherein the at least two first outer pulleys are aligned to provide a substantially straight longitudinal line path for a portion of the second pitch/slider cable to follow between the first outer pulley and the first side of the second pitch axis pulley; and wherein the at least two second outer pulleys are aligned to provide a substantially straight longitudinal line path for a portion of the second pitch/slider cable to follow between the second outer pulley and the second side of the second pitch axis pulley.

* * * * *